(12) United States Patent
Smith et al.

(10) Patent No.: US 11,543,407 B2
(45) Date of Patent: Jan. 3, 2023

(54) FLEXIBLE OPTICAL BIOSENSOR FOR POINT OF USE MULTI-PATHOGEN DETECTION

(71) Applicant: ARIZONA BOARD OF REGENTS ON BEHALF OF ARIZONA STATE UNIVERSITY, Scottsdale, AZ (US)

(72) Inventors: Joseph Smith, Tempe, AZ (US); Jennifer Blain Christen, Chandler, AZ (US); Karen Anderson, Scottsdale, AZ (US); Benjamin Katchman, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 1520 days.

(21) Appl. No.: 15/308,330

(22) PCT Filed: May 1, 2015

(86) PCT No.: PCT/US2015/028734
§ 371 (c)(1),
(2) Date: Nov. 1, 2016

(87) PCT Pub. No.: WO2015/168515
PCT Pub. Date: Nov. 5, 2015

(65) Prior Publication Data
US 2017/0059563 A1    Mar. 2, 2017

Related U.S. Application Data

(60) Provisional application No. 62/127,154, filed on Mar. 2, 2015, provisional application No. 61/986,977, filed on May 1, 2014.

(51) Int. Cl.
*G01N 33/543*     (2006.01)
*B01L 3/00*       (2006.01)
(Continued)

(52) U.S. Cl.
CPC ...... *G01N 33/54366* (2013.01); *A61B 5/0071* (2013.01); *A61B 5/6802* (2013.01);
(Continued)

(58) Field of Classification Search
CPC ......... G01N 33/54366; G01N 21/6428; G01N 21/6454; G01N 33/54373;
(Continued)

(56) References Cited

U.S. PATENT DOCUMENTS 5,321,790 A * 6/1994 Takahashi ............ G02B 6/2552
                                                385/123
7,046,357 B2 * 5/2006 Weinberger ....... B01L 3/502715
                                                250/216
(Continued)

FOREIGN PATENT DOCUMENTS

EP       3105590 A1     12/2016
WO    2007141700 A2     12/2007
(Continued)

OTHER PUBLICATIONS

Lefevre et al. (Lab Chip, 2012, 12, 787). (Year: 2012).*
(Continued)

*Primary Examiner* — Jill A Warden
(74) *Attorney, Agent, or Firm* — Quarles & Brady, LLP

(57) ABSTRACT

A fully integrated miniaturized optical biosensor and methods of making the same are disclosed. The biosensor may include a fluid transport system and an optical system.

9 Claims, 13 Drawing Sheets

(51) Int. Cl.
  *G01N 21/64* (2006.01)
  *G01N 21/05* (2006.01)
  *A61B 5/00* (2006.01)
(52) U.S. Cl.
  CPC ... *B01L 3/502707* (2013.01); *B01L 3/502715* (2013.01); *B01L 3/502761* (2013.01); *G01N 21/6428* (2013.01); *G01N 21/6454* (2013.01); *G01N 33/54373* (2013.01); *B01L 2200/025* (2013.01); *B01L 2200/12* (2013.01); *B01L 2300/0636* (2013.01); *B01L 2300/0654* (2013.01); *B01L 2300/087* (2013.01); *B01L 2300/0819* (2013.01); *B01L 2300/0825* (2013.01); *B01L 2300/123* (2013.01); *G01N 21/05* (2013.01); *G01N 2021/6439* (2013.01); *G01N 2201/0221* (2013.01)
(58) Field of Classification Search
  CPC ... G01N 2021/6439; G01N 2201/0221; G01N 21/05; B01L 3/502761; B01L 3/502707; B01L 3/502715; B01L 2200/025; B01L 2200/12; B01L 2300/0819; B01L 2300/087; B01L 2300/123; B01L 2300/0825; B01L 2300/0654; B01L 2300/0636; A61B 5/0071; A61B 5/6802
  See application file for complete search history.

(56) References Cited

U.S. PATENT DOCUMENTS

| | | | |
|---|---|---|---|
| 9,741,742 B2 | 8/2017 | Smith | |
| 10,170,407 B2 | 1/2019 | Smith | |
| 10,249,741 B2 | 4/2019 | Smith | |
| 2002/0008871 A1 | 1/2002 | Poustka | |
| 2003/0164295 A1 | 9/2003 | Sterling | |
| 2004/0234417 A1 | 11/2004 | Schienle | |
| 2005/0157301 A1 | 7/2005 | Chediak et al. | |
| 2006/0181700 A1* | 8/2006 | Andrews | G01N 21/474 356/237.2 |
| 2007/0231922 A1 | 10/2007 | Petruno | |
| 2008/0003664 A1 | 1/2008 | Tysoe et al. | |
| 2010/0096563 A1* | 4/2010 | Ponjee | G01J 1/58 250/459.1 |
| 2010/0136521 A1* | 6/2010 | Yoon | G01N 33/543 13 435/5 |
| 2010/0141938 A1 | 6/2010 | Banerjee et al. | |
| 2016/0181182 A1 | 6/2016 | Smith | |
| 2016/0287898 A1 | 10/2016 | Smith | |
| 2016/0331994 A1 | 11/2016 | Smith | |
| 2018/0172681 A1 | 6/2018 | Katchman | |
| 2018/0186066 A1* | 7/2018 | Cooper | B33Y 10/00 |

FOREIGN PATENT DOCUMENTS

| | | |
|---|---|---|
| WO | 2014031157 A1 | 2/2014 |
| WO | 2015156862 A2 | 10/2015 |
| WO | 2016195918 A1 | 12/2016 |
| WO | 2018208610 A1 | 11/2018 |

OTHER PUBLICATIONS

International Search Report and Written Opinion dated Jul. 28, 2015 in connection with PCT/US2015/028734.
Anderson K.S., et al., "Application of Protein Microarrays for Multiplexed Detection of Antibodies to Tumor Antigens in Breast Cancer," Journal of Proteome Research, vol. 7, pp. 1490-1499, Apr. 1, 2008 2008.
Anderson K.S., et al., "Autoantibody Signature for the Serologic Detection of Ovarian Cancer," Journal of Proteome Research, 2014.
Anderson K.S., et al., "Protein Microarray Signature of Autoantibody Biomarkers for the Early Detection of Breast Cancer," Journal of Proteome Research, vol. 10, pp. 85-96, Jan. 1, 2011 2010.
Anderson N.L. et al., "The human plasma proteome: history, character, and diagnostic prospects," Mol Cell Proteomics, vol. 1, pp. 845-867, Nov. 2002.
Bandodkar A. J. et al., "Non-invasive wearable electrochemical sensors: a review," Trends in Biotechnology, vol. 32, pp. 363-371.
Banerjee A., et al., "Concentration dependence of fluorescence signal in a microfluidic fluorescence detector," Journal of Luminescence, vol. 130, pp. 1095-1100.
CLEAR Blue Easy Pregnancy Test. (2014). Available: http://www.clearblueeasy.com/advanced-pregnancy-test-with-weeks-estimator.php.
Colglazier E., "Remarks on Global Water Security," 46th Session of the Erice International Seminars: Role of Science in the Third Millenium, 2013.
Derbyshire. (2013). A thin, flexible and fully integrated biosensor for the detection of lactate in human sweat. Available: http://elsevier.conference-services.net/resources/247/2514/pdf/BITE2011_0381.pdf.
Dixit R., et al., "Simultaneous Single Detector Measurement of Multiple Fluorescent Sources," Sensors Journal, IEEE, vol. 13, pp. 1965-1971, 2013.
D'Souza, G., et al. "Oral human papillomavirus (HPV) infection in HPV-positive patients with oropharyngeal cancer and their partners." Journal of Clinical Oncology 32.23 (2014): 2408.
Dupont Teijin Films Teonex® PEN Film for Flexible Displays and Electronics. (2013). Available: http://www2.dupont.com/Displays/en_US/products_services/films/PEN_film.html.
European Patent Office, Extended European Search Report, application EP15786337.4, dated Nov. 27, 2017.
Haq J., et al., "Temporary Bond Debond process for manufacture of Flexible Electronics: Impact of Adhesive and Carrier Properties on Performance," Journal of Applied Physics, vol. 108, p. 114917, 2010.
Heikenfeld J. (2014) Sweat Sensors Will Change How Wearables Track Your Health—IEEE Spectrum. IEEE Spectrum. Available: http://spectrum.ieee.org/biomedical/diagnostics/sweat-sensors-will-change-how-wearables-track-your-health.
Knight S.L., et al., "Establishing predictive indicators for the status of loaded soft tissues," J Appl Physiol (1985), vol. 30, pp. 2231-2237, Jun. 2001.
Lee, L., et al. "A low-cost, high-performance system for fluorescence lateral flow assays." Biosensors 3.4 (2013): 360-373.
Marrs M., et al., "Flexible amorphous silicon PIN diode x-ray detectors," in Proc. SPIE 8730, Flexible Electronics, 2013, pp. 87300C-87300C-7.
Miersch, S. et al. "Nucleic acid programmable protein arrays: Versatile tools for array-based functional protein studies." Current protocols in protein science 64.1 (2011): 27-2.
O'brien B., et al., "14.7" Active Matrix PHOLED Displays on Temporary Bonded PEN Substrates with Low Temperature IGZO TFTs," SID Symposium Digest of Technical Papers, vol. 70-2L, p. 447, 2013.
Pais A., et al. "High-sensitivity, disposable lab-on-a-chip with thin-film organic electronics for fluorescence detection," Lab Chip, vol. 8, pp. 794-800, May 2008.
Peters R., "Water rights," The Daily Californian, Monday May 13, 2013, accessed online at https://www.dailycal.org/2013/05/13/water-rights/ on Aug. 27, 2019.
Petricoin E., et al., "Clinical proteomics: revolutionizing disease detection and patient tailoring therapy," J Proteome Res, vol. 3, pp. 209-217, Mar.-Apr. 2004.
Ramachandran N., et al., "Next-generation high-density self-assembling functional protein arrays," Nat Meth, vol. 5, pp. 535-538, 06//print 2008.
Ryu, G., et al. "Highly sensitive fluorescence detection system for microfluidic lab-on-a-chip." Lab on a Chip 11.9 (2011): 1664-1670.
Sarma K.R., "Active Matrix OLED Using 150C a-Si TFT Backplane Built on Flexible Plastic Substrate," SPIE Symp. on Aerospace/Defense Sensing, vol. 580, p. 180, 2003.
Seiler C.Y., et al., "DNASU plasmid and PSI:Biology-Materials repositories: resources to accelerate biological research," in Nucleic Acids Res. vol. 42, ed, 2014, pp. D1253-D1260.

(56) References Cited

OTHER PUBLICATIONS

Sibani S. et al., "Immunoprofiling Using NAPPA Protein Microarrays," in Protein Microarray for Disease Analysis. vol. 723, C. J. Wu, Ed., ed: Humana Press, 2011, pp. 149-161.

Smith J., "Disposable Point-of-Use Optical Biosensor for Multiple Biomarker Detection," presented at the BioCAS 2014, 2014.

Smith J., et al., "Flexible Digital x-ray technology for far-forward remote diagnostic and conformal x-ray imaging applications," Proc. SPIE 8730, Flexible Electronics, 2013.

Smith J., et al., "Flexible ISFET Biosensor Using IGZO Metal Oxide TFTs and an ITO Sensing Layer," Sensors Journal, IEEE, vol. PP, pp. 1-1, 2013.

Smith J.T., et al., "Application of Flexible OLED Display Technology for Electro-Optical Stimulation and/or Silencing of Neural Activity," Display Technology, Journal of, vol. PP, pp. 1-1, 2014.

DigiKey—TEMD6010FX01 Vishay Semiconductor Opto Division | 751-1051-2-ND | DigiKey. (2014). Available: http://www.digikey.com/product-detail/en/TEMD6010FX01/751-1051-2-ND/1681185.

Wagner S. et al., "Materials for stretchable electronics," MRS Bulletin, vol. 37, pp. 207-213, 2012.

Wilkinson C., et al., "Enhanced performance of pulse driven small area polyfluorene light emitting diodes," Applied Physics Letters, vol. 79, p. 171, 2001.

Wulfkuhle J., et al., "New approaches to proteomic analysis of breast cancer," Proteomics, vol. 1, pp. 1205-1215, Oct. 2001.

DolceraWiki—OLED Mobile Phones Market Research and Analysis Report. (2014). Available: http://www.dolcera.com/wiki/index.php?title=OLED_Mobile_Phones_Market_Research_and_Analysis_Report.

Lefevre, Florent, et al. "Algal fluorescence sensor integrated into a microfluidic chip for water pollutant detection." Lab on a Chip 12.4 (2012): 787-793.†

\* cited by examiner
† cited by third party

FLEXIBLE OPTICAL BIOSENSOR FOR POINT OF USE MULTI-PATHOGEN DETECTION

CROSS-REFERENCE TO RELATED APPLICATIONS

This application represents the national stage entry of PCI International Application No. PCT/US2015/028734, entitled "FLEXIBLE OPTICAL BIOSENSOR FOR POINT OF USE MULTI-PATHOGEN DETECTION," filed on May 1, 2015, and claims priority to U.S. Provisional Patent Application No. 61/986,977, filed May 1, 2014, and U.S. Provisional Patent Application No. 62/127,154, filed Mar. 2, 2015, the entire contents of which are hereby incorporated by reference in their entirety.

STATEMENT REGARDING FEDERALLY SPONSORED RESEARCH

N/A

BACKGROUND

The disclosure relates generally to multi-pathogen fluorescent biosensors.

In an increasingly unhealthy and aging population, more frequent and/or continuous home monitoring of patients with multiple chronic conditions is expected to be key for more effective disease self-management and improve patient care—along with maintaining and supporting a healthy and independent lifestyle. One promising approach to help make health care both more affordable and more accessible is to replace a portion of existing high cost medical diagnostic testing with simple to use, low cost, and disposable point-of-care biosensors. These point-of-care devices reduce diagnostic costs by eliminating the need for sophisticated and expensive laboratory equipment combined with eliminating the need for trained medical staff to perform the diagnostic tests, which can be done instead by either the patient at home or by a health care worker with very limited training in a non-clinical setting such as at a pharmacy.

Fluorescence based detections systems utilize fluorophore labeled primary or secondary antibodies to visualize and identify specific proteins of interest. In this respect, researchers are able to transition this technology for use in minimally invasive biomarker discovery and downstream clinical use. Human sera, along with other human biofluids (sweat, saliva, tears, urine, etc.) contain proteins, peptides, and autoantibodies that can be utilized for the early identification of specific diseases as well as following disease progression and regression. Standard fluorescence based detection systems utilize antibodies that are specific for one protein or peptide. The antibodies are first chemically labeled (tagged) with a fluorophore and then allowed to dock or bind with a target antigen immobilized on the surface of cells, tissue, or antigens coated on a downstream reaction chamber. The binding of an antibody with its antigen of interest is referred to as an immunocomplex.

This antibody immunocomplex, formed by the paired (docked) antibodies and antigens, is proportional to the concentration of antibodies in the original sample. Selectivity is provided by the labeled antibodies only binding with a specific antigen. After allowing time for binding, the reaction (detection) chamber containing the bound antigen/antibodies pairs is then illuminated with light of a specific wavelength. The fluorophore labels attached to the antibodies absorb the incident light and then re-emit light (i.e., fluoresce) at a slightly longer wavelength, typically about 30 to 50 nm longer. For example, a fluorophore illuminated with green light would typically emit yellow-orange light. The re-emitted light intensity is then measured using a photodetector to determine the antibody concentration in the sample. Higher emitted light intensity generated by more docked pairs corresponds to a higher antibody concentration in the sample. This optical diagnostic technique is typically called an immunoassay and enables specific antibodies to be detected in the original sample by using an antigen targeted for only the corresponding antibody.

Unfortunately, existing low cost and fully disposable point-of-care sensors for health monitoring have limited sensitivity and can only detect a single disease or pathogen biomarker in patient biofluid samples. For example, typical colorimetry-based lateral flow immunoassay (LFIA) pregnancy test strips require a relatively high concentration of the protein hCG in women's urine to ensure the colored test line is visible to the human eye. More sensitive and sophisticated diagnostic testing currently requires a trip to a doctor's office or clinical laboratory. One way to significantly improve point-of-care sensitivity is to use fluorescent-based biorecognition instead of colorimetry. For low cost and ultimately disposable configurations, multiple researchers have reported on a compact fluorescence measurement-based configuration using a microfluidic detection layer sandwiched between an organic light emitting diode (OLED) emitter and solid state photodetector. An OLED emitter is used to replace the laser light source used in typical laboratory fluorescent measurement instrumentation, while the photodetector replaces the low light digital camera. One key limitation of these reported disposable devices is the inability to detect the fluorescent signal emitted from more than a single biomarker. Additionally, poor light attenuation through the orthogonally crossed polarizers in existing configurations was also observed to significantly limit biosensor sensitivity by almost three orders of magnitude—rendering these reported devices ineffective in providing clinical level sensitivity.

Another promising diagnostic approach is the integration of biosensors into a skin patch. In existing implementations, human sweat is typically collected and channeled to the inlet of the microfluidics layer to start the diagnostic sequence. Reported skin patch-style biosensors have primarily focused on real-time physiological monitoring of electrolytes and metabolites in the sweat of athletes or military personnel using electrochemical sensing. However, given their molecular composition and low concentration in both sweat and human sera, the detection of biomarkers associated with chronic diseases requires bioaffinity immobilization as opposed to electrochemical detection. An enzyme-linked immunosorbent assay (ELISA) using fluorescent biorecognition is one well known and proven bioaffinity-based technique with the required sensitivity to detect multiple biomarkers in sweat, saliva, and human sera. However, ELISA-type testing has traditionally required transporting the biofluid sample to a remote diagnostic laboratory for analysis.

Another of the key roadblocks limiting the transition of high sensitivity fully disposable point-of-care technologies from the research laboratory to wide spread field or home use is the availability of a low cost high volume manufacturing technology.

Consequently, considering such limitations of previous technological approaches, it would be desirable to have a system and method for portably detecting or quantifying a plurality of analytes of interest in a fluid sample suspected of containing the plurality of analytes of interest. It would further be desirable if the sensitivity of this system and method could reach clinical level sensitivities, similar to the sensitivies of lab-based solutions. Finally, it would be desirable to develop systems and methods that utilize technology that is currently being manufactured in high volumes, in order to take advantage of the economies of scale associated with those high volumes, and to thus produce devices at a low cost.

SUMMARY

The present disclosure overcomes the aforementioned drawbacks by presenting apparatuses and methods for multi-pathogen detection in a portable apparatus.

The disclosure described herein is intended to function as a miniaturized fluorescence microscopy laboratory able to detect signals at diagnostically relevant levels.

In one aspect, this disclosure provides an apparatus for detecting or quantifying a plurality of analytes of interest in a fluid sample suspected of containing the plurality of analytes of interest may include a microfluidic or nanofluidic system and an optical system. The microfluidic or nanofluidic system may include a sample inlet for receiving the sample; a mixing chamber for mixing the sample with one or more selective binding fluorescent labels; a detection chamber comprising a first volume and a second volume, the first volume comprising a first immobilized selective binding species and the second volume comprising a second immobilized selective binding species; and a sample outlet, wherein the sample inlet, the mixing chamber, the detection chamber, and the sample outlet are fluidly connected. The optical system may include a light source, a detector, and a means of attenuating radiation from the light source at the detector. The light source may be configured to illuminate the first volume and the second volume. The detector may be configured to receive and detect emitted radiation from the first volume and the second volume. The apparatus may be operable to detect or quantify a first analyte of interest and a second analyte of interest by meeting one of the following conditions: the first immobilized selective binding species selectively binds the first analyte of interest and not the second analyte of interest and the second immobilized selective binding species binds the second analyte of interest and not the first analyte of interest; a first selective binding label selectively binds the first analyte of interest and not the second analyte of interest and the second selective binding label selectively binds the second analyte of interest and not the first analyte of interest; the light source is configured to illuminate the first volume with light having a first illumination spectrum and the second volume with light having a second illumination spectrum; or the detector is configured to receive and detect emitted radiation from the first volume having a first emission spectrum and emitted radiation from the second volume having a second emission spectrum.

In another aspect of the present disclosure, a method of making an apparatus may comprise positioning an active matrix thin-film transistor display and an active matrix thin-film transistor photodiode opposite one another with a separation ranging from about 1 nm to about 10 mm; and positioning a detection chamber of a microfluidic or nanofluidic system between the display and the photodiode.

In yet another aspect of the present disclosure, a method of making an apparatus may comprise positioning an active matrix thin-film transistor display and an active matrix thin-film transistor photodiode on a flexible or rigid substrate; manipulating the flexible or rigid substrate to position the display and photodiode opposite one another with a separation ranging from about 1 nm to about 10 mm; and positioning a detection chamber of a microfluidic or nanofluidic system between the display and the photodiode. In certain aspects, the substrate is a flexible substrate.

In a further aspect of the present disclosure, a biomarker detection device using a apparatus can include a fluorescent biorecognition microarray disposed in a microfluidics layer and configured to capture the biomarker from a biofluid, an organic light emitting diode (OLED) array aligned with the fluorescent biorecognition microarray and configured to emit light of a desired wavelength onto the fluorescent biorecognition microarray, and a photodiode array aligned with the fluorescent biorecognition microarray on an opposite side of the fluorescent biorecognition microarray from the OLED array and configured to receive light emitted from the biomarker. The fluorescent biorecognition microarray may be produced using flat panel display technology. The fluorescent biorecognition array, the OLED array, and the photodiode array may all be modularized into a test strip, and the device may include multiple test strips. The device may include a charge integration circuit in electrical communication with the photodiode array and configured to convert a charge produced by one or more photodiodes of the photodiode array into a voltage.

In another aspect of the present disclosure, a biomarker detection device having a fluorescent biorecognition microarray can be produced using flat panel display technology, which may include one or more excitation optical filters aligned with the fluorescent biorecognition microarray in a position to filter light incident on the fluorescent biorecognition microarray, and may further include one or more emission optical filters aligned with the fluorescent biorecognition microarray in a position to filter light emitted by the fluorescent biorecognition microarray. The excitation and emission optical filters may be compatible with the flat panel display technology of the fluorescent biorecognition microarray. The device may further include a microfluidics layer in fluid communication with the fluorescent biorecognition microarray such that a lateral flow of a biofluid across the microfluidics layer draws one or more biomarkers in the biofluid into the fluorescent biorecognition microarray. The microfluidics layer may transmit between about 10% and about 100% of visible light. The device may further include a flexible display configured to display signals produced by the fluorescent biorecognition microarray. This device may be a wearable bandage containing the flexible display and the fluorescent biorecognition microarray.

In yet another aspect of the present disclosure, a biomarker detection device can be configured to detect a plurality of different pathogens using a single disposable biosensor having a plurality of biorecognition sites disposed on a single lateral flow membrane. The biorecognition sites may be configured into a fluorescent biorecognition array that converts incident light from one wavelength to another and emits the converted light if pathogens are present. The lateral flow membrane may be optically transparent to allow light to impinge the biorecognition sites. The lateral flow membrane may be incorporated into a microfluidics layer. The biosensor may be disposable due to its low cost as a result of high-volume production using flat panel display technology.

The foregoing and other aspects and advantages of the disclosure will appear from the following description. In the description, reference is made to the accompanying drawings which form a part hereof, and in which there is shown by way of illustration a preferred aspect of the disclosure. Such aspect does not necessarily represent the full scope of the disclosure, however, and reference is made therefore to the claims and herein for interpreting the scope of the disclosure. It should be appreciated that the aspects of the disclosure are not mutually exclusive, and certain aspects can be combined with other aspects, despite not being explicitly described in combination with one another.

DETAILED DESCRIPTION

Before the present disclosure is described in further detail, it is to be understood that the disclosure is not limited to the particular aspects described. It is also to be understood that the terminology used herein is for the purpose of describing particular aspects only, and is not intended to be limiting. The scope of the present disclosure will be limited only by the claims.

As used herein, the singular forms "a", "an", and "the" include plural aspects unless the context clearly dictates otherwise.

Specific structures, devices, transistors, and methods relating to flexible optical biosensors have been disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Aspects referenced as "comprising" certain elements are also contemplated as "consisting essentially of" and "consisting of" those elements.

This disclosure provides a fully integrated miniaturized optical biosensor that is designed to detect multiple biomarkers or pathogens in a sample at the point of use. The biosensor configuration is designed to be both inexpensive to manufacture and disposable after use.

Figure 1:
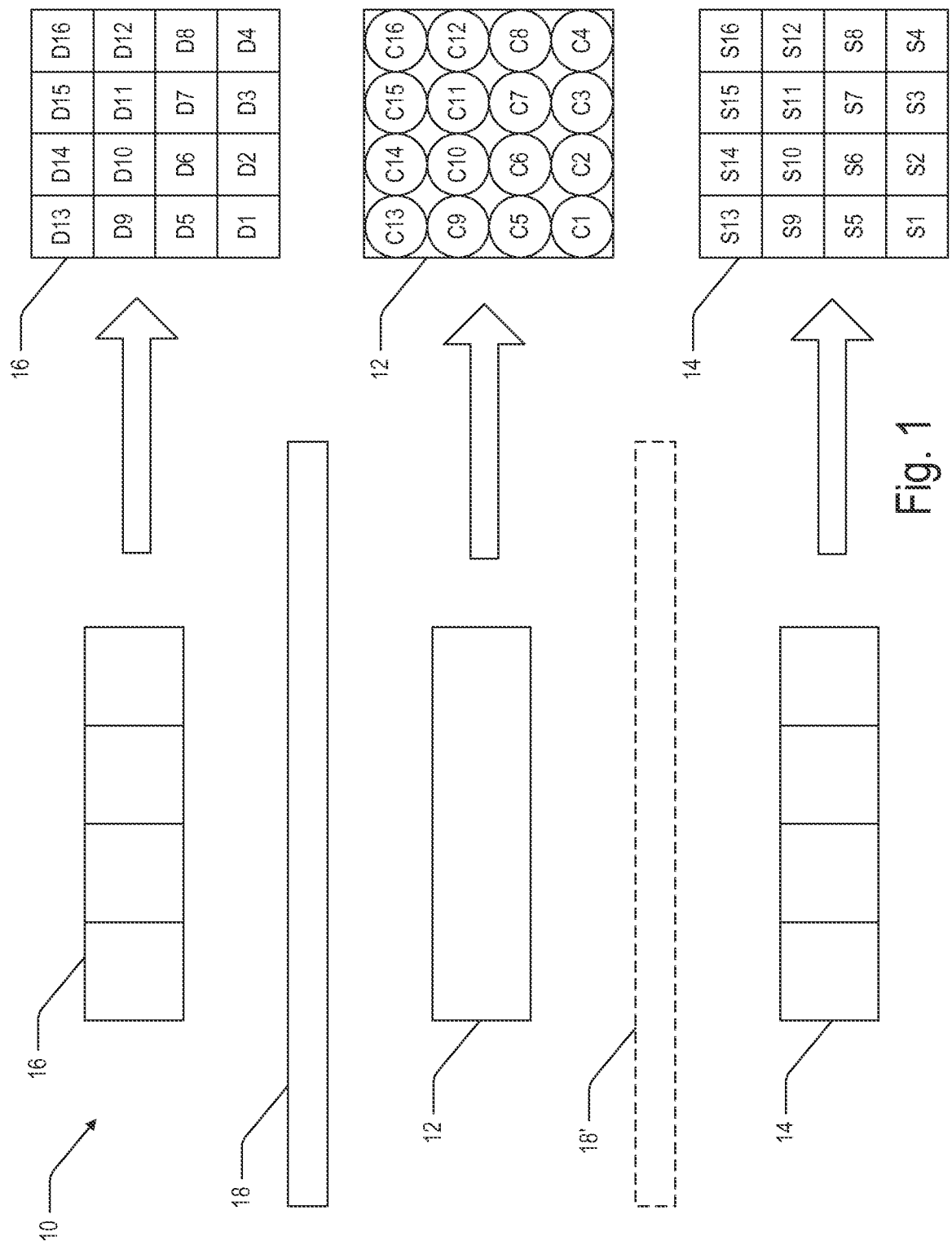
FIG. 1 is a schematic representation of an apparatus, in accordance with one aspect of the present disclosure.

Referring to FIG. 1, in one aspect of this disclosure, an apparatus 10 is provided for on-site detection of a plurality of analytes of interest in a fluid of interest suspected of containing one or more of the plurality of analytes of interest. The apparatus can include a fluid transport system and an optical system. The fluid transport system system can include a detection chamber 12. The optical system can include a light source 14, an optical detector 16, and a light source attenuator 18. The apparatus is arranged such that light from the light source 14 illuminates the detection chamber 12, and fluorescence from the detection chamber 12 passes through the light source attenuator 18 and impinges on the optical detector 16 for detection. The elements of the apparatus are shown on the left of FIG. 1 from the side in a blown apart configuration and on the right of FIG. 1 from the top. It should be appreciated that the elements shown on the left of FIG. 1 can be arranged to be in contact with one another, separated by small gaps, or other configurations that retain the functionality of the apparatus, while maintaining a small size fingerprint that is optimal for on-site sensing.

The detection chamber 12 can be a microfluidic or a nanofluidic chamber. The detection chamber 12 can include a plurality of selective binding sites C1-C16. The plurality of selective binding sites C1-C16 can include immobilized selective binding species. The immobilized selective binding species can selectively bind an analyte of interest, thereby immobilizing the analyte of interest at the selective binding site. In certain aspects, the detection chamber 12 can be a fluorescent biorecognition microarray.

The light source 14 can be an array of individual light sources S1-S16, such as organic light-emitting diodes (OLEDs). In some aspects, the light source 14 can be a flat panel display, an array of OLEDs, an active matrix thin film transistor array, a flexible display array, or a combination thereof. In some aspects, the light source can be a flexible OLED array.

The optical detector 16 can be an array of individual optical detectors D1-D16, such as individual photodiodes. In some aspects, the optical detector 16 can be an array of PiN photodiodes. In some aspects, the optical detector 16 can include an active matrix thin film transistor array. In some aspects, the optical detector 16 can be a flexible PiN photodiode sensor active matrix array.

The light source attenuator 18 can be a single component that attenuates light from the light source for the entirety of the optical detector 16 (as illustrated in FIG. 1) or can be a series of individual elements, each element attenuating light from the light source for a single individual optical detector D1-D16.

As shown in FIG. 1, the apparatus 10 can also include a second attenuation optic 18'. In some aspects, the apparatus 10 can only include the light source attenuator 18, in the form of a filter that filters light having the characteristics of the light from the light source 14. In some aspects, the apparatus 10 can include a polarizer as the second attenuation optic 18' and a crossed polarizer as the light source attenuator 18. In some aspects, the apparatus 10 can include as the second attenuation optic 18' a filter that allows much of the light from the light source to pass, but filters out wavelengths of light that overlap with the fluorescence emission spectrum of a selective binding label. In some aspects, the light source attenuator 18 can a long-pass filter, where the wavlelength cutoff is such that the light from the light source is filtered. In some aspects, the second attenuation optic 18' can be a bandpass filter that allows a desired wavelength In some aspects, the second attenuation optic 18' is a single optic spanning the entirety of the light source (i.e., covering each element of the light source array). In some aspects, the second attenuation optic 18' can be a plurality of attenuation optics, each covering a subset of the light source, including but not limited to, a plurality of attenuation optics, each covering a single pixel of the light source array. In some aspects, the light source attenuator 18 can be a single optic spanning the entirety of the optical detector (i.e., covering each element of the optical detector array). In some aspects, the light source attenuator 18 can be a plurality of attenuation optics, each covering a subset of the optical detector, including but not limited to, a plurality of attenuation optics, each covering a single pixel of the optical detector array.

In addition to the aforementioned configurations, the light source 14 or optical detector 16 of the present disclosure can be adapted to contain a filter, a polarizer, or a combination thereof that covers a single pixel of the light source 14 or a single photodiode of the optical detector 16. For example, with respect to the source, a blue OLED pixel may be fitted with a short pass optical filter that only passes blue light and blocks green light, while a green OLED pixel may be fitted with a short pass optical filter that only passes green light and blocks orange. With respect to the detector, a PiN photodiode pixel oriented opposite a blue OLED pixel may be fitted with a long pass optical filter, which blocks blue light and passes weak green light emitted by a fluorophore, while a PiN photodiode pixel oriented opposite a green OLED pixel may be fitted with a long pass optical filter, which blocks green light and passes weak orange light emitted by a fluorophore.

In certain aspects, a filter element may be printed directly on the emission surface of a pixel of the source or on a detection surface of a PiN photodiode of the detector. A non-limiting example of a means of printing a filter element directly on a pixel of the source or on a PiN photodiode of the detector is printing a color gel optical filter directly on the surface of the pixel or photodiode.

The detection chamber 12, the light source 14, and the optical detector 16 can each be an array as shown in FIG. 1 (right). It should be appreciated that a single array size is shown in FIG. 1, but larger or smaller arrays are contemplated. The detection chamber 12 can be an array of selective binding sites, labeled C1-C16 in FIG. 1. The light source 14 can be an array of OLED emitters, labeled S1-S16 in FIG. 1. The optical detector 16 can be an array of photodiodes, labeled D1-D16 in FIG. 1. The arrays can be aligned with one another such that light emitted from OLED emitter S1 illuminates selective binding site C1, and fluorescence emitted from selective binding site C1 impinges on photodiode D1. The same is true for similarly numbered OLED emitters, selective binding sites, and photodiodes.

In addition to the detection chamber, the fluid transport system can include a sample inlet, a mixing section, and a sample outlet. The fluid transport system can be microfluidic, nanofluidic, or a combination thereof.

The sample inlet serves to receive the fluid sample and to provide the fluid sample to the mixing section or the detection chamber. In some aspects, the sample inlet can be a sample pad.

The mixing section can serve two functions. First, the mixing section can store a plurality of selective binding labels. Second, the mixing section can serve as a volume in which the analytes of interest can be sufficiently mixed with the plurality of selective binding labels. In some aspects, the mixing section can be a mixing chamber In some aspects, the mixing section can be a conjugate pad.

In some aspects, the sample inlet and the mixing section can be a single component where the sample is received and the analytes of interest are mixed with one or more selective binding labels.

The sample outlet serves to receive the fluid sample from the detection chamber. In some aspects, the sample outlet is a fluid wick that is in fluid communication with the detection chamber.

The apparatus 10 can include a power supply, such as a battery, configured to provide power to the components of the apparatus.

The apparatus 10 can include a processor, configured to receive and interpret signals from the optical detector 16.

One approach to add multiple pathogen or biomarker detection is to increase the number of paired light sources and photodetectors. For example, one could envision an 8×8 array of discrete light sources paired with an 8×8 array of opposing discrete photodetectors to detect for 64 different biomarkers or pathogens. Between each of the 64 paired light sources and opposing photodetectors would be 64 different immobilized antigen spots in the microfluidic detection chamber.

However, a key downside with this approach is the size of an array using conventional discrete components can quickly get quite large as well as expensive, which is an issue for disposable applications. For example, an 8×8 array of Vishay TEMD6010FX01 miniature surface mount PiN photodiodes (photodetectors), each of which has a footprint of 4×2×1.5 mm (L×W×H), will require a printed circuit board (PCB) between one and two inches in diameter. At 70 cents each (cost in volume as of the time of drafting), 64 individual TEMD6010FX01's mounted on a PCB will now cost almost 50 dollars. An 8×8 array of surface mount LEDs will be similarly large and costly. Although, three single color (red, green, and blue) LEDs would likely work in combination with simple optics, as opposed to using an array of LEDs. However, with either discrete electronic component approach, the microfluidic detection chamber will still be greater than 1 inch in diameter. This in an order of magnitude larger in fluid volume than typical low cost disposable blotter paper-based microfluidics. To compensate for the increased fluid volume, one alternative to absorbent blotter paper-based microfluidics is to add a squeeze bulb at the end of the unit to give the higher starting fluid volume an initial boost. For small starting sample volumes, such as blood from a finger stick, dilution fluid could also be provided to increase the initial sample volume using separate integrated microfluidic chamber. The valves to the microfluidic dilution chamber could be set to automatically burst open and flow from the pressure applied by the squeeze bulb. While this discrete component based approach is relatively straightforward, these extra components will clearly increase the sensor unit cost and size, as well as increase the fragility, making the desired low disposable sensor concept for multi-pathogen detection—not so disposable, not so miniaturized, or more importantly, not so low cost.

The light source may comprise a display having multiple pixels capable of generating distinct frequencies of light. In certain aspects, the light source or the optical detector may comprise active matrix, thin-film transistor (TFT) array technology. In TFT array technology, the typical flat panel display pixel or PiN photodiode pixel is approximately 200 µm. Hence, an 8×8 array of 64 pixels using active matrix display technology is now less than 2 mm instead of one to two inches. This is now small enough to work with the limited sample volumes eliminate the need for the separate squeeze bulb and dilution fluid chamber.

Figure 2:
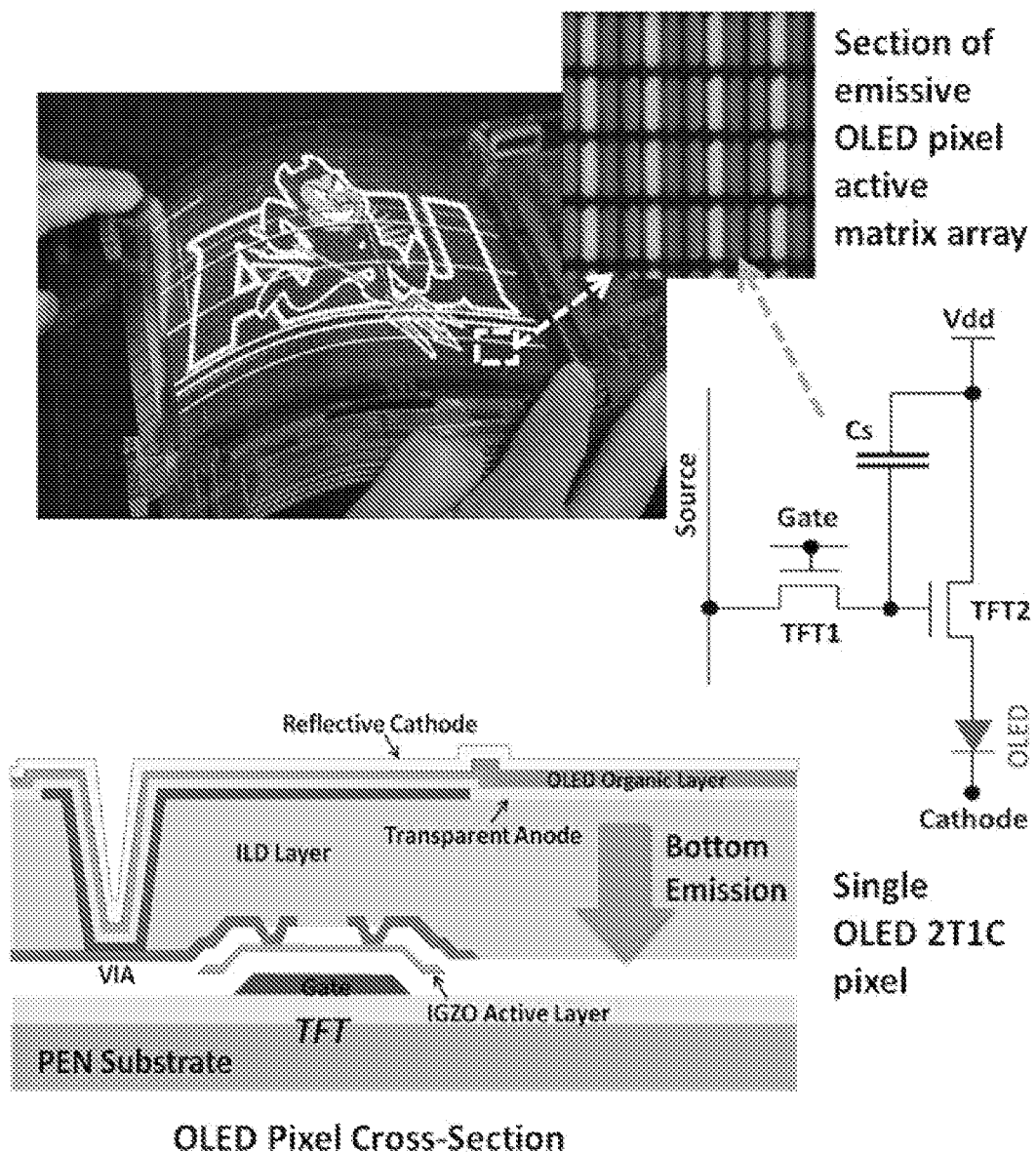
FIG. 2 shows an image of a color OLED display on a flexible plastic substrate (top, main), with a small region magnified to highlight the individual pixels (top, inset), the circuit schematic for a two-transistor, one-capacitor (2T1C) pixel utilized in the display (right), and a schematic cross-section of a pixel (bottom), including the structure for both the bottom emitting OLED and TFT.

The light source may comprise organic light emitting diode (OLED) display technology. As shown in FIG. 2, an OLED display consists of an array of emissive light emitting elements, typically called pixels. The OLED pixel shown includes two thin film transistors (TFTs) and a capacitor, which are used provide the ability to individually address (i.e., turn on) each OLED pixel in the array [14]. The thin OLED organic layer shown in FIG. 2 emits a bright light when a forward voltage bias is applied across the transparent anode and reflective cathode terminal, with the color of the emitted light a function of the materials in the OLED organic layer, and the brightness a function of the current.

In operation, the OLED pixels in the active matrix array may be activated (turned on) sequentially to separately illuminate each of the separate immobilized antigen regions or spots in the combination microfluidic reaction and detection chamber. At the same time each of the OLED pixels is activated sequentially, opposing PiN photodiodes in a separate photodiode active matrix array will also be sequentially selected and the detected optical signal for each individual photodiode read out and recorded using a separate CMOS integrated circuit.

Figure 3:
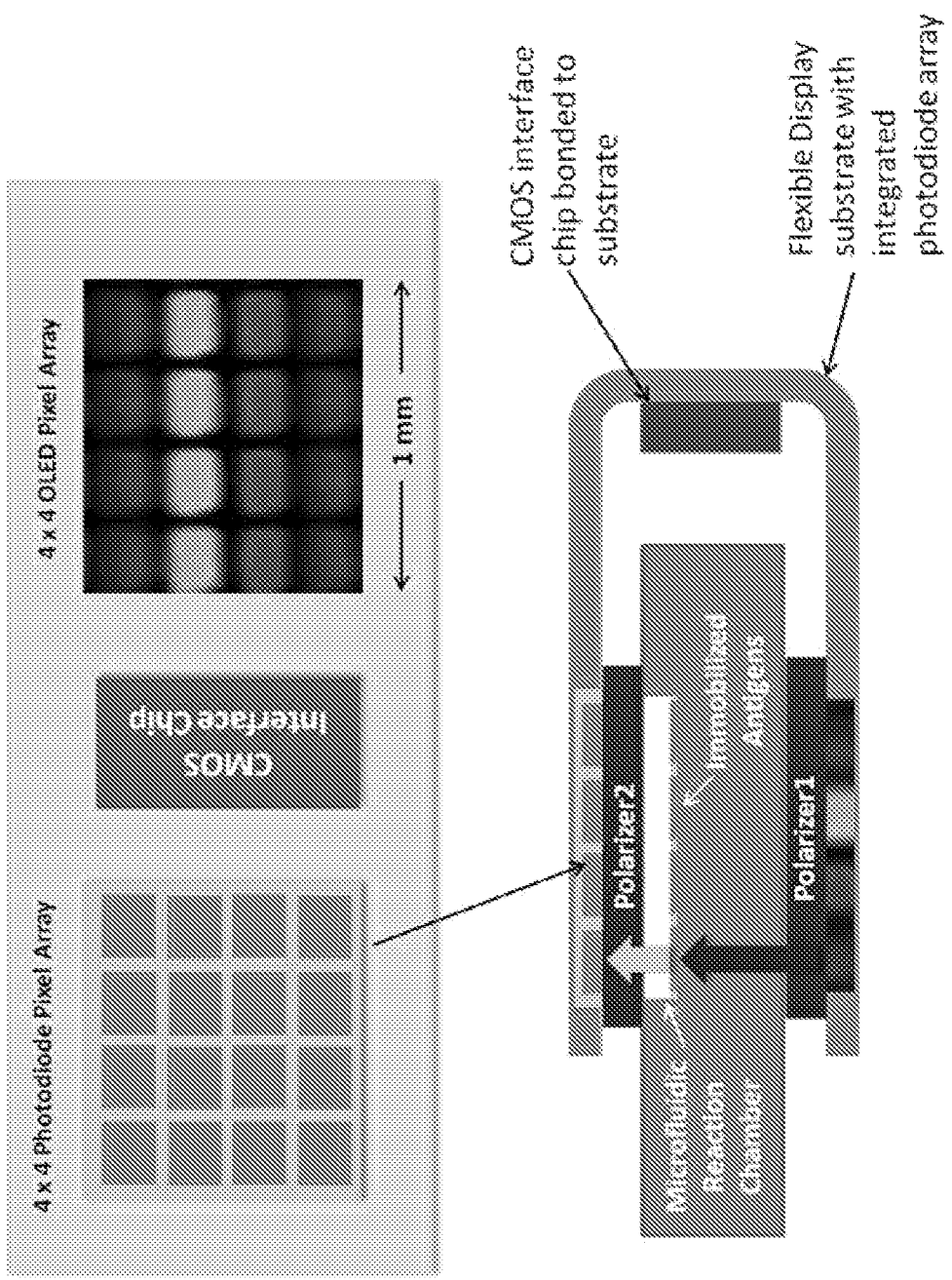
FIG. 3 shows a flexible substrate with a 4×4 photodiode pixel array, a CMOS interface chip, and a 4×4 OLED pixel array oriented on the surface (top), and a cross-section of the flexible substrate manipulated to orient the photodiode array and pixel array opposite one another with a microfluidic reaction chamber positioned between (bottom).

This sequential illuminate and readout operation is illustrated in FIG. 3, where one of the blue OLEDs is activated (turned on) in the 16 pixel 4×4 active matrix array. The blue light is absorbed by the labeled fluorophores and is then re-emitted as longer wavelength blue-green light. Again, the crossed linear polarizers block the (bright blue) light from source from reaching the selected single photodiode pixel and masking the weak (blue-green) light emitted from the fluorophore.

The detector may comprise a PiN photodiode pixel array. At the conceptual level, the PiN photodiode pixel array is essentially a digital camera. Light emitted by the fluorophore provides the illumination, and the photodiode array functions similarly to the solid state CMOS or CCD imager in a digital camera. However, unlike CCDs or CMOS imagers, which use silicon wafer semiconductor processing, a conventional a PiN photodiode detector array is typically manufactured using thin film transistor (TFT) technology on large glass substrates—similar to the process used to manufacture large area flat panel liquid crystal displays (LCDs). To make the PiN photodiode detector array flexible, the substrate may comprise a polymer. In preferred aspects, the substrate may comprise a 125 µm thick, flexible, and extremely tough polyethylene naphthalate (PEN) plastic substrate from DuPont.

Figure 4:
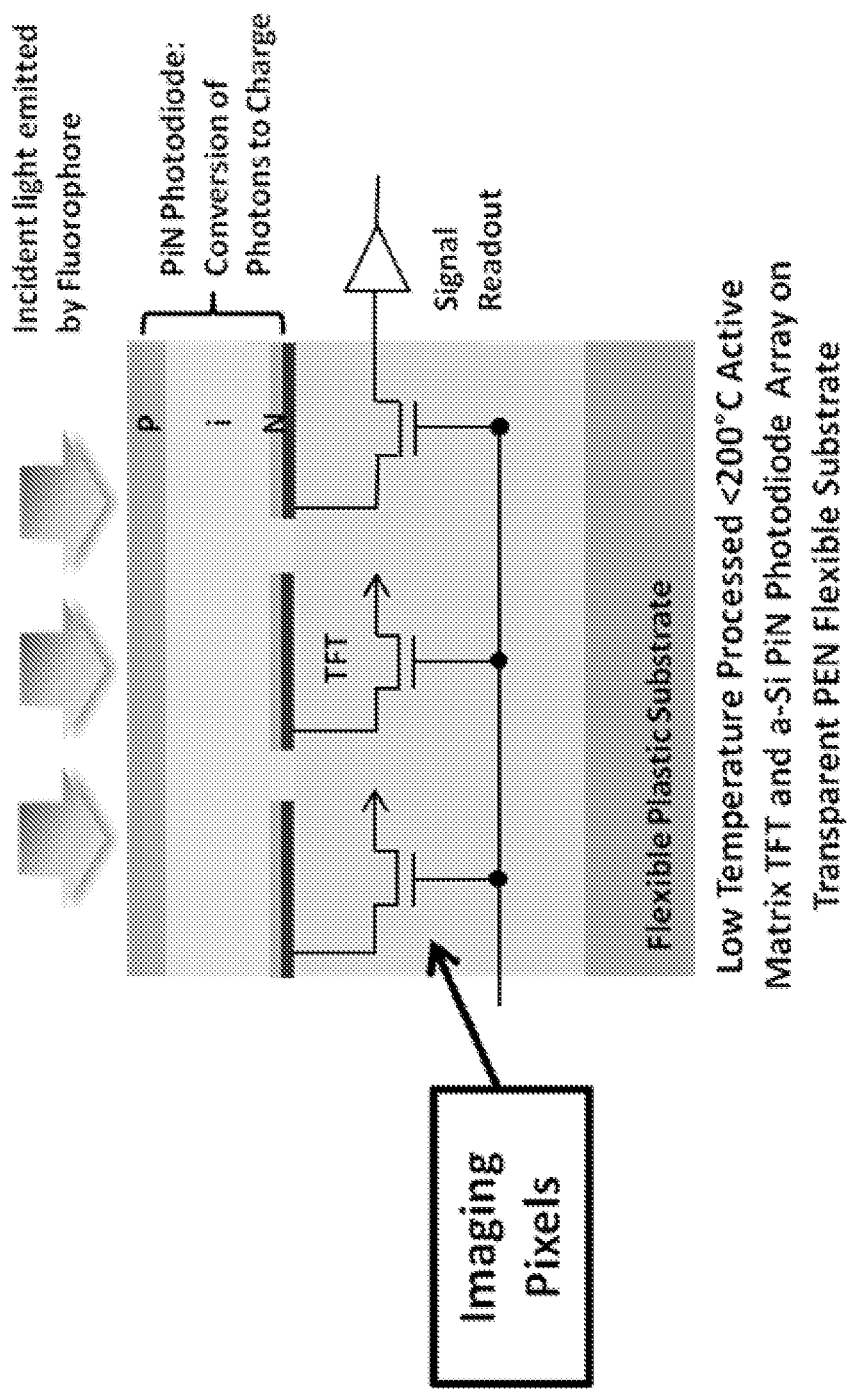
FIG. 4 shows a schematic representation of a flexible photodiode detector array architecture.

As illustrated in FIG. 4, the flexible PiN photodiode detector array can be fabricated on a flexible plastic substrate covered by an active matrix array of imaging pixels. Each pixel in the active matrix array may have one TFT transistor and a PiN photodiode. The TFT functions as an on/off switch that electrically connects the photodiode to a dataline when the gate line is asserted by a large positive voltage. The pixel PiN photodiode is essentially a miniature photovoltaic solar cell, which converts incident photons into electrical charge or current proportional to incident light intensity.

To simplify the configuration and reduce the number of components required, the light source (for example, the OLED array) and optical detector (for example, the photodiode array) may be fabricated on the same flexible electronics substrate, as shown in FIG. 3 with the 4×4 pixel array. The CMOS interface circuit (chip) may be bonded to the flexible substrate with the integrated 4×4 display and photodiode array. Substrate flexibility may allow this single integrated electronics assembly to be bent or wrapped around the microfluidic chamber as shown in FIG. 3 to position the OLED and opposing photodiode pixels in a pitch matched face-to-face configuration. In addition to simplifying the sensor electronics to just one integrated and flexible assembly, a flexible electronic substrate may also more rugged than a rigid substrate along with being thinner and more compact than a discrete component assembly.

In terms of cost as a function of display size, commercial OLED display technology currently costs about 80 cents/$cm^2$. Even with the addition of peripheral circuitry, input/outputs (I/O's), plus the opposing PiN photodiode array—less than a few square centimeters of display substrate area may be required for each multi-pathogen disposable sensor. This keeps the projected sensor component cost for the integrated OLED display and photodiode active matrix array on the flexible electronics substrate to less than 2 dollars, which is estimated to be more than an order of magnitude cheaper than a comparable configuration using discrete components.

Figure 5:
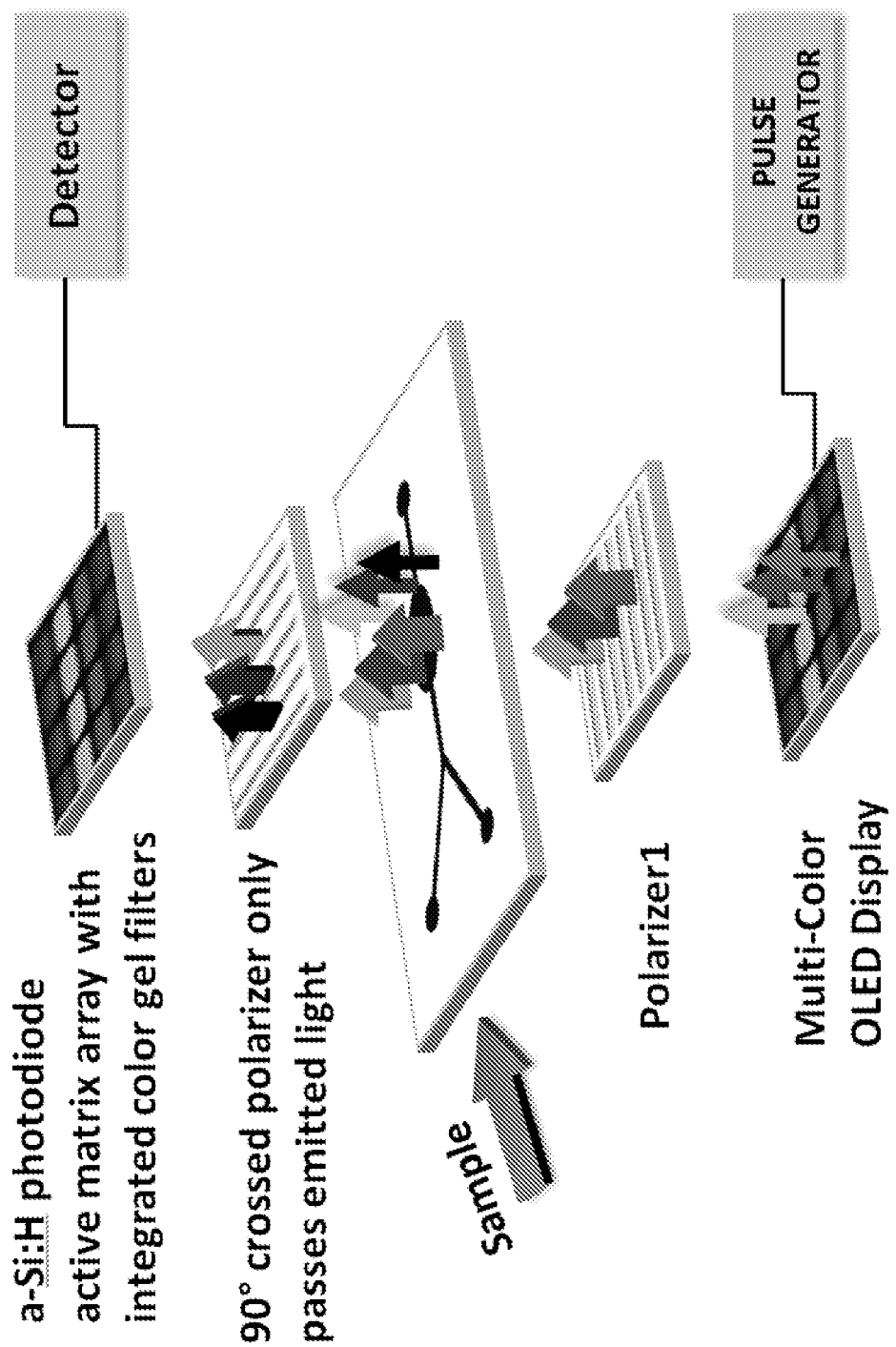
FIG. 5 shows a schematic representation of one aspect of the apparatus of the present disclosure, blown apart to make individual components more clear.

FIG. 5 shows a schematic representation of an aspect of the apparatus of the present disclosure. The light source can be a 4×4 multicolor (Red/Green/Blue) OLED pixel array. The detector is a 4×4 photodiode array. This combination enables the detection of at least 16 different pathogens and/or disease biomarkers. It should be noted that a 4×4 pixel array is shown for convenience only and the arrays can have higher resolution. It should further be noted that the microfluidic system and the optical system are not drawn to scale in FIG. 5. In an actual device, the array size may more closely match the dimensions of the microfluidic detection chamber.

Figure 6:
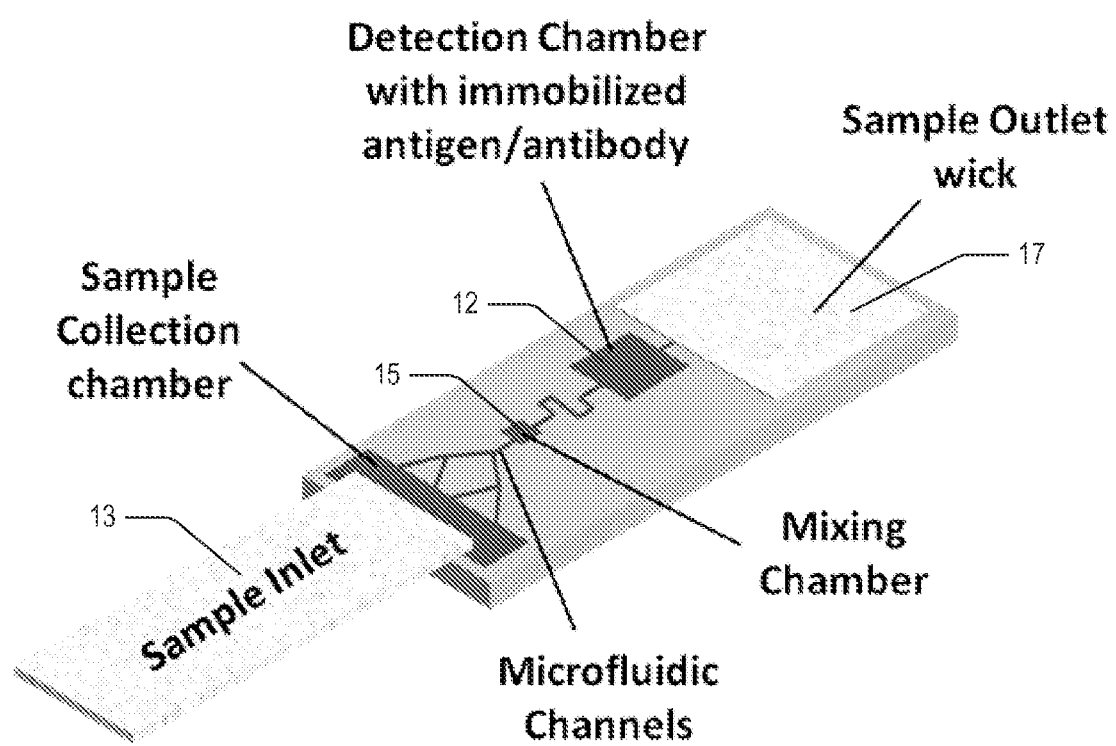
FIG. 6 shows a schematic representation of one aspect of the microfluidic assembly of the apparatus of the present disclosure.

Referring to FIG. 6, the microfluidic or nanofluidic system may comprise: a sample inlet 13 for receiving the sample; a mixing chamber 15 for mixing the sample with one or more selective binding fluorescent labels; a detection chamber 12 comprising a first volume and a second volume, the first volume comprising a first immobilized selective binding species and the second volume comprising a second immobilized selective binding species; a sample outlet 17; or a combination thereof.

In certain aspects, the nanofluidic or microfluidic system of the present disclosure may have a configuration similar to that shown in FIG. 6. In this simplified configuration, the starting (liquid) sample may be collected using a highly absorbent piece of blotter paper that is attached to sample collection chamber at the inlet of the disposable microfluidic assembly (FIG. 6). In typical operation, the user may place the blotter paper in the sample of interest, such as a glass of water or a sample of biofluid. The water or biofluid may then absorbed by the blotter paper and collected in the integrated microfluidic sample collection chamber to start the lab on a chip style diagnostic process sequence. Passive capillary action may draw the fluid sample from the collection chamber through the microfluidic channels towards the down stream detection chamber. As shown in FIG. 6, after the collection chamber, the starting sample first enters a mixing chamber, where the liquid sample reconstitutes dried fluorescent labeled antibody or antigen beads placed in the mixing chamber during the initial microfluidic assembly process [4].

A serpentine channel, immediately down stream from the mixing chamber, may then be used to delay the sample and provide enough time for the antigen/antibody reaction between the sample and the dried fluorescent labeled antibody to complete before reaching the downstream detection chamber. When the now fluorescently labeled sample reaches the detection chamber, it may be captured by a second antibody immobilized on the surface of the detection chamber to complete the identification of the biomarkers or pathogens in the starting sample. A downstream sample outlet wick, which can be as simple as a large and thick piece of blotter paper, may then be used to draw off any excess fluid as well as clear the detection chamber of un-reacted material. As described previously, the detection chamber may be sequentially illuminated by each OLED pixel in the array and the concentration of each antigen or antibody present in the sample may be proportional to the intensity of light emitted from the labeled antibody/antigen immunocomplex that is detected by the opposing PiN photodiode pixel.

Figure 7:
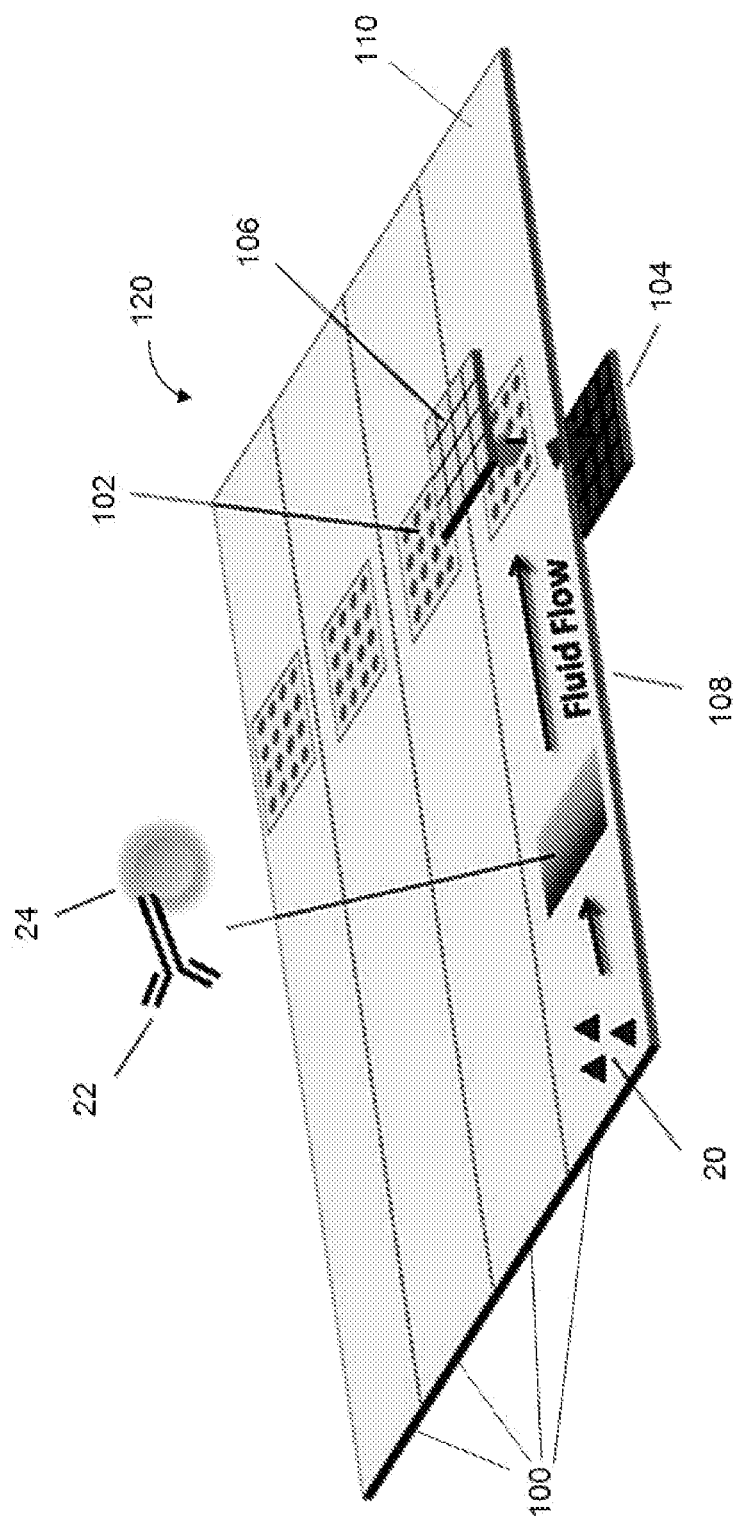
FIG. 7 is a perspective diagram of an embodiment of four adjacent modules of an apparatus, in accordance with the present disclosure.

Referring to FIG. 7, the apparatus 100 combines flexible electronics and display technology with protein display and detection technology to enable the detection of one or more disease and pathogen biomarkers 20 in patient biofluid samples. The apparatus 100 integrates ELISA-type high density fluorescent biorecognition microarray 102 with a flexible OLED array 104 (i.e., a light source) and a PiN photodiode sensor active matrix array 106 (i.e., an optical detector) technology into a single thin and flexible assembly on a microfluidic layer 110, such as a transparent nanoporous membrane. The PiN photodiodes may be any suitable type of photodiode having the required sensitivity, such as a-Si:H PiN or organic PiN photodiodes.

In a fluorescent-based LFIA (F-LFIA) configuration, proteins of interest 20 are first tagged with a fluorophore 24 delivered by a secondary antibody 22 as the proteins 20 pass by capillary action through a conjugate pad 112 on the microfluidic layer 110. Capillary action further draws the biofluid toward the downstream biorecognition sites of the microarray 102 deposited (printed) on the microfluidic layer 110. The arrays 102, 104, 106 together enable detection of multiple biomarkers, while the fluorescent biorecognition microarray 102 further provides diagnostic laboratory sensitivity when combined with low cost optical filters instead of the previously reported orthogonally crossed linear polarizers. The apparatus 100 effectively miniaturizes much of the functionality found in a typical medical diagnostic laboratory into a small, very inexpensive (less than $5), fully disposable configuration. Compared to existing point-of-care disposable devices, the present array-based apparatus 100 increases the number of detectable biomarkers 20 by >10× and diagnostic sensitivity by >100×.

To maximize economies of scale, the apparatus 100 may be manufactured in a uniform process even when the devices that use the apparatus 100 implement it in different ways. Distinct modules of the apparatus 100, referred to herein as "test strips" as an analogy to known disposable immunosensors, may be manufactured in large (i.e., table top sized) flexible electronic sheets or layers, which may then be bonded or laminated together to form the complete biosensor assembly. The sensing assembly for a particular device may then be cut or punched out of the sheet. In particular, while other implementations of the apparatus 100 are envisioned, the present disclosure describes in detail two devices that illustrate the adaptability of the apparatus 100. A "finger stick" device for fingerstick-type testing of multiple biomarkers in human sera uses a single module of the apparatus 100 as a sensor, referred to herein as a "test strip." A "bandage" or "skin patch" device for continuously and non-invasively monitoring biomarkers in a biofluid, such as sweat, uses a linear array (e.g., test strip array 120 of FIG. 7) of a plurality of test strips. For fingerstick point-of-care applications, individual complete test strips would then be punched out, while for smart bandage-type multi-test strip applications, 10 to 20 adjacent test strips would be punched out as one unit.

Figure 8:
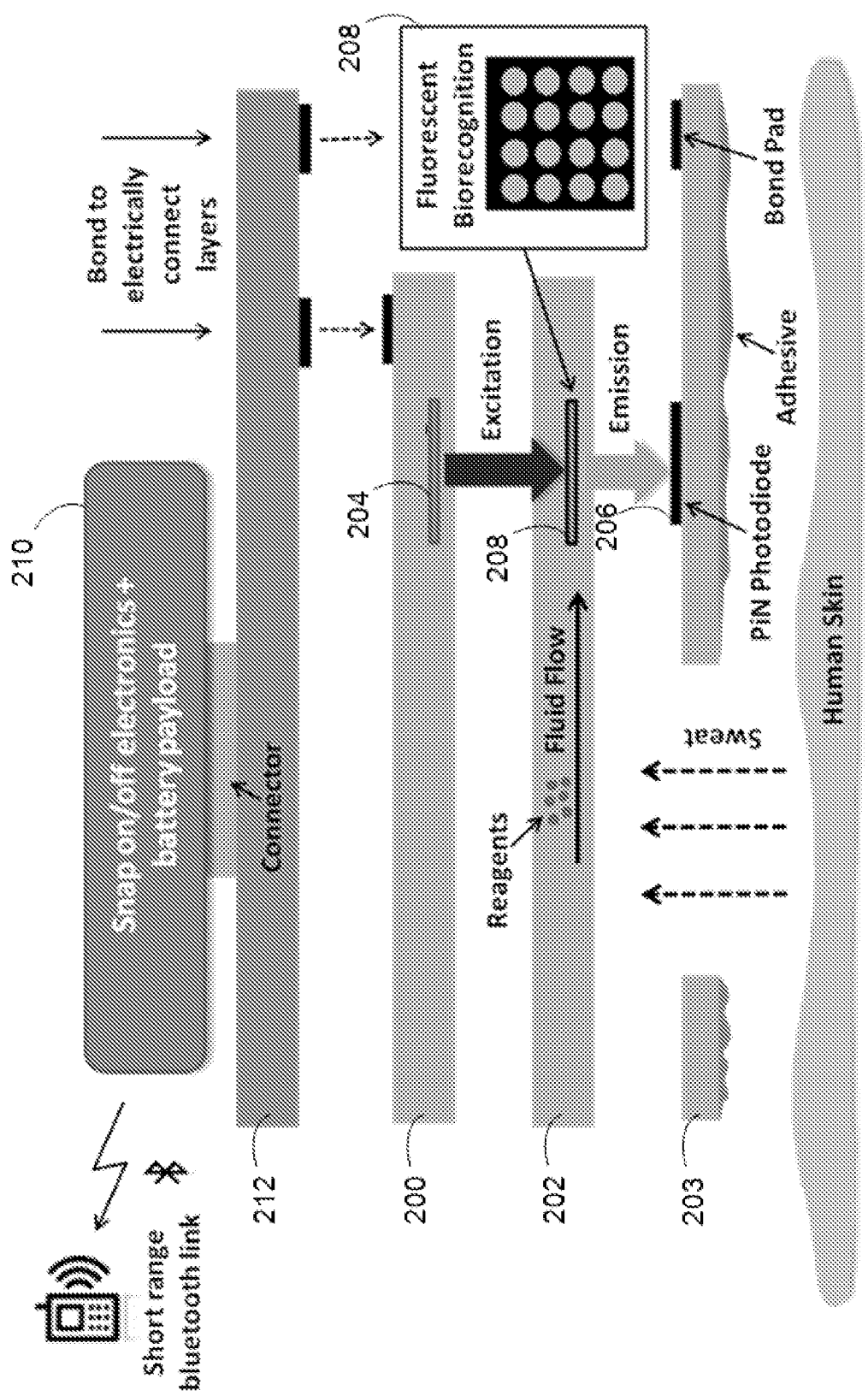
FIG. 8 is a schematic diagram of the apparatus of FIG. 7.

Referring to FIG. 8, one configuration of the apparatus 100 includes a thin microfluidics layer 202 disposed between a flex OLED layer 200 containing an array 204 of OLED (light) emitters, and a flex photodiode layer 206 containing a PiN photodiode (light detecting) array 206. To increase the number of detectable biomarkers, an individual OLED pixel of the OLED array 204 is paired with an opposing PiN photodiode of the photodiode array 206 for each biomarker. In the illustrated example, a 4×4 array 204 of individual light sources (OLED pixels) is paired with an opposing 4×4 array 206 of photodiodes. Using this configuration, up to 16 individual biomarkers may be detected when used in combination with 16 separate biorecognition sites printed on the microfluidics layer 202 using protein display and detection technology. In operation, the emissive OLED pixels in an array 204 will be activated (turned on) sequentially to illuminate each of the immobilized fluorescent biorecognition sites in a fluorescent biorecognition microarray 208 on the lateral flow membrane pad of the microfluidics layer 202. At the same time each of the OLED pixels is activated sequentially, opposing PiN photodiode pixels in the separate photodiode active matrix sensor array 206 will also be sequentially selected and the detected optical signal from each individual photodiode is read out and recorded using an external CMOS integrated circuit. The OLED array 204 and photodiode array 206 may be electrically connected to the CMOS integrated circuit and a power source, both represented by the snap on/off electronics and battery payload 210, by an interconnect 212, such as a two-layer passive flex interconnect.

Assuming a 5×5 cm sized patch for the collection area, a minimum of several hundred micro-liters of human sweat should be collectable during a 30 to 60 minute sample interval. An integrated thin film micro-actuator (not shown) is used to connect the larger sweat collection chamber with one of the individual sensors in a multi-sensor array. After giving the tagged proteins enough time to bind to the downstream capture antibody sites, the backside of the fluorescent biorecognition microarray 208 is now illuminated by, for example, blue light emitted by a blue OLED. Any illuminated fluorescent material captured on the printed biorecognition sites now re-emits longer wavelength green light (for a blue excite/green emit fluorophore tag). The emitted green light then passes through a long pass optical filter (not shown), where it is detected by a photodiode, while the shorter wavelength light from the blue OLED is blocked from reaching the photodiode by the same long pass optical filter. This sandwich style optics configuration prevents the weak fluorescence signal from being swamped out by bright blue light from the OLED emitter, and is key to providing point-of-care diagnostic sensitivity that approaches the capabilities of a clinical laboratory.

Figure 9:
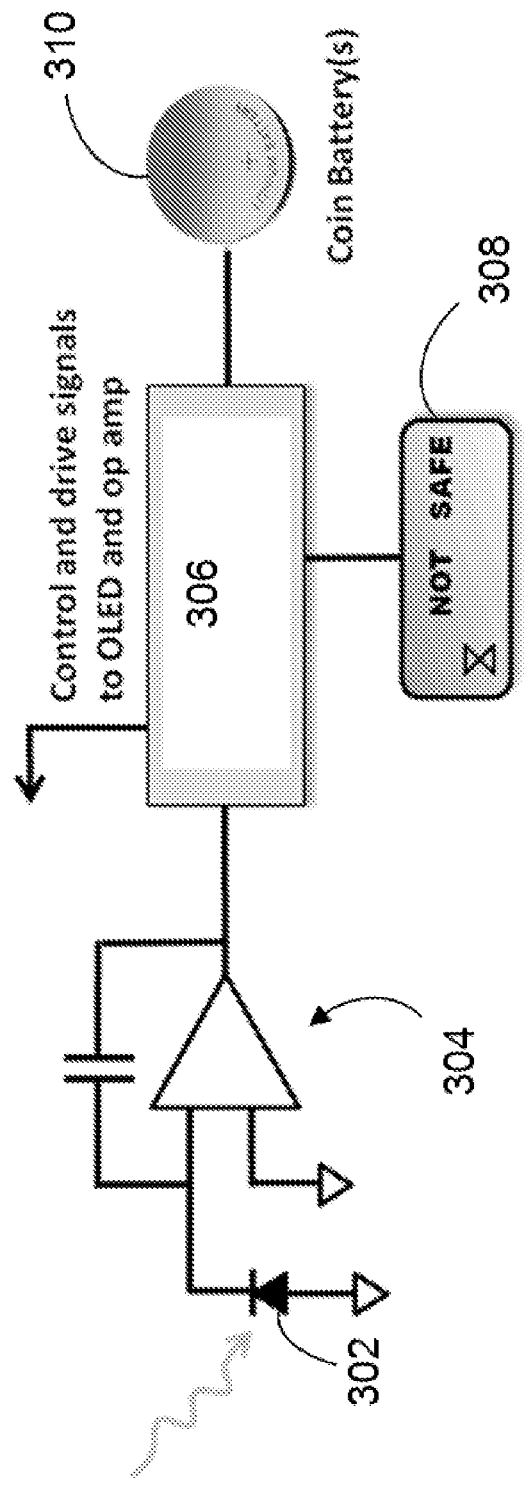
FIG. 9 is a diagram of a charge integration circuit for processing signals from a photodiode, in accordance with an aspect of the present disclosure.

Referring to FIG. 9, a simplified electronics block diagram shows the signal processing of a single photodiode 302 from the photodiode array. The photodiode 302 may be connected in photovoltaic mode to minimize the effects of dark current. Upon incidence of the green light emitted by the fluorescent material, the output of the photodiode is directed to a low noise op-amp charge integration circuit 304, which converts the detected charge from the photodiode 302 to a voltage which can be read by a microprocessor 306 operated by a battery 310. For analysis, the detected signal level at the input to the microprocessor 306 is now directly proportional to the concentration of the protein biomarkers in the biofluid sample. After some internal digital signal processing, the microprocessor 306 can then directly translate the detected input signal level from the photodiode 302 to actionable user information. This information may be displayed on a display 308 (e.g., a tiny LCD display) of the point-of-care device or sent via Bluetooth to a smartphone. An advantage of this system is the ability to use long op-amp charge integration times (~1 minute per site) to detect extremely low light levels from a very small number of fluorophores captured by the primary antibody. Additionally, this configuration only requires a few low cost components to achieve high sensitivity, adding only a few dollars to the overall point-of-care system cost.

Figure 10:
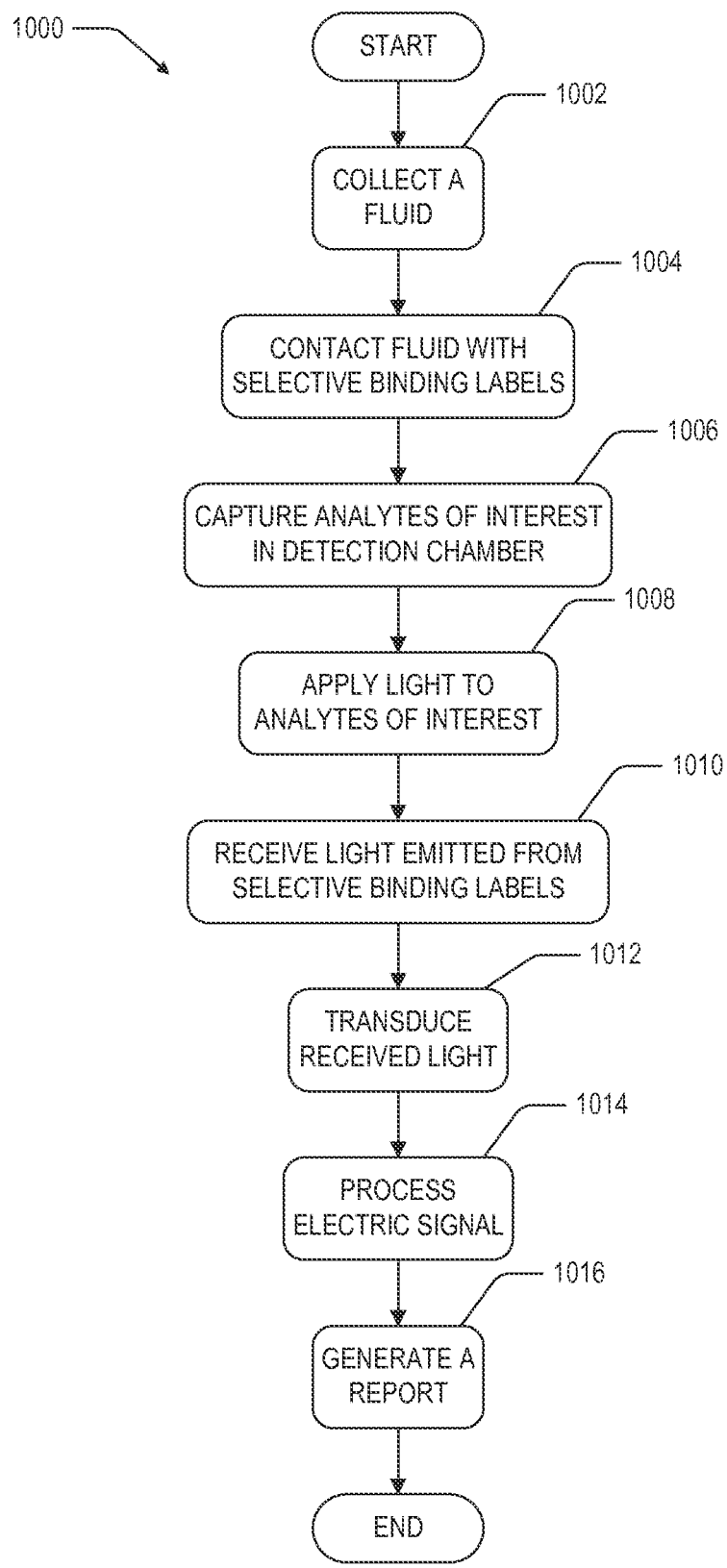
FIG. 10 is a flowchart illustrating a method of operation of a device implementing the apparatus described herein, in accordance with an aspect of the present disclosure.

Referring to FIG. 10, a flowchart describing a method 1000 of detecting one or more analytes of interest in a fluid suspected of containing an analyte of interest is shown. At process block 1002, the method 1000 can include collecting a fluid. At process block 1004, the method 1000 can include contacting the fluid with selective binding labels, thereby applying selective binding labels to the one or more analytes of interest. At process block 1006, the method 1000 can include capturing the one or more analytes of interest in a detection chamber. In certain aspects, process block 1006 can include the use of selective binding species that are immobilized in the detection chamber. The selective binding species can be located in individual cells of an array that are aligned with a pixel of the light source and a pixel of the optical detector. Multiple different selective binding species can be used. Different selective binding species can be placed in different locations, based on experimental needs. At process block 1008, the method 1000 can include applying light from the light source to the analytes of interest that are bound by a selective binding label and are bound to a selective binding species. At process block 1010, the method 1000 can include receiving light emitted from the selective binding labels at the optical detector. At process block 1012, the method 1000 can include tranducing the received light into an electric signal. At process block 1014, the method 1000 can include processing the electric signal. At process block 1016, the method 1000 can include generating a report including the processed signal.

Figure 11:
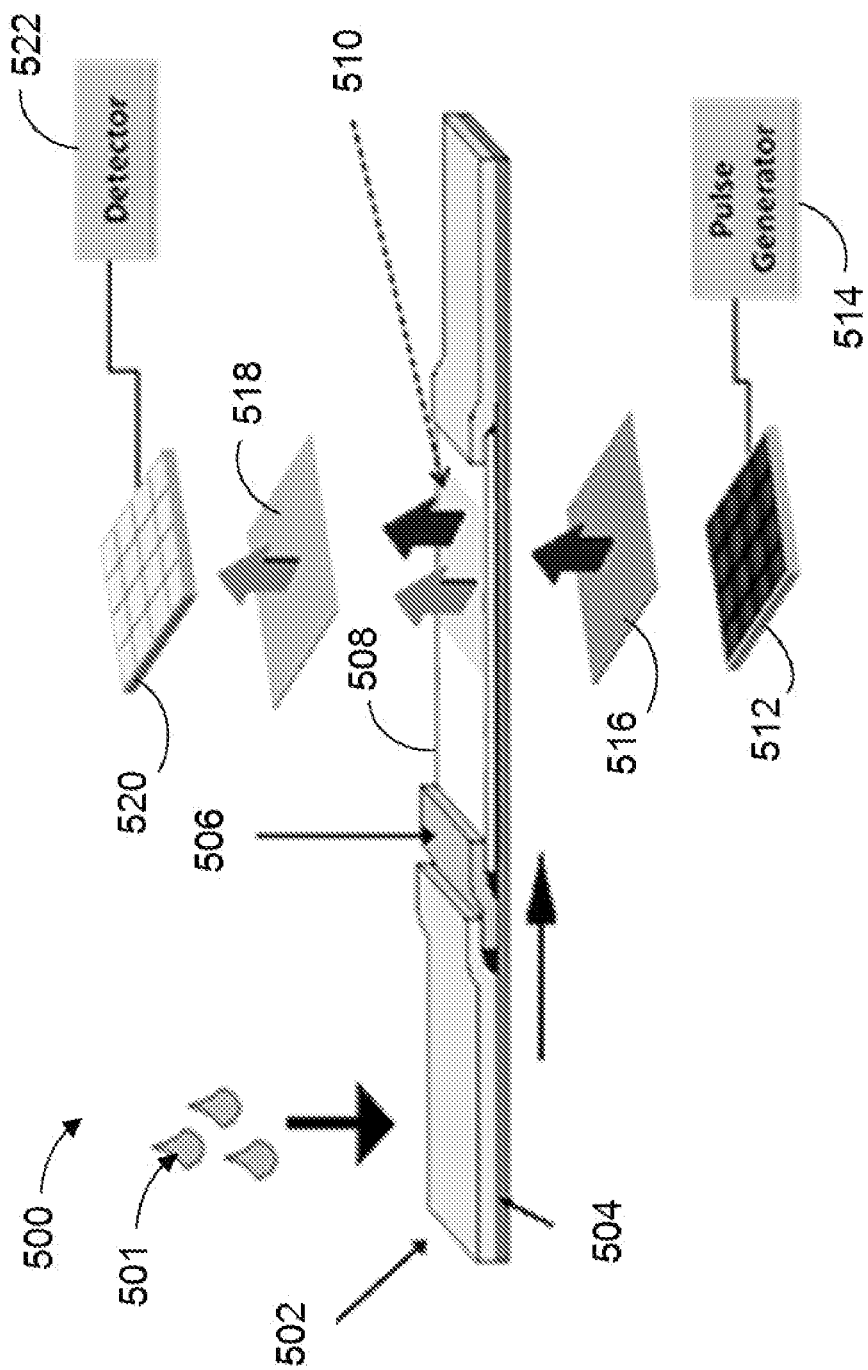
FIG. 11 is an exploded perspective view of a test strip including an apparatus, in accordance with an aspect of the present disclosure.
Figure 12:
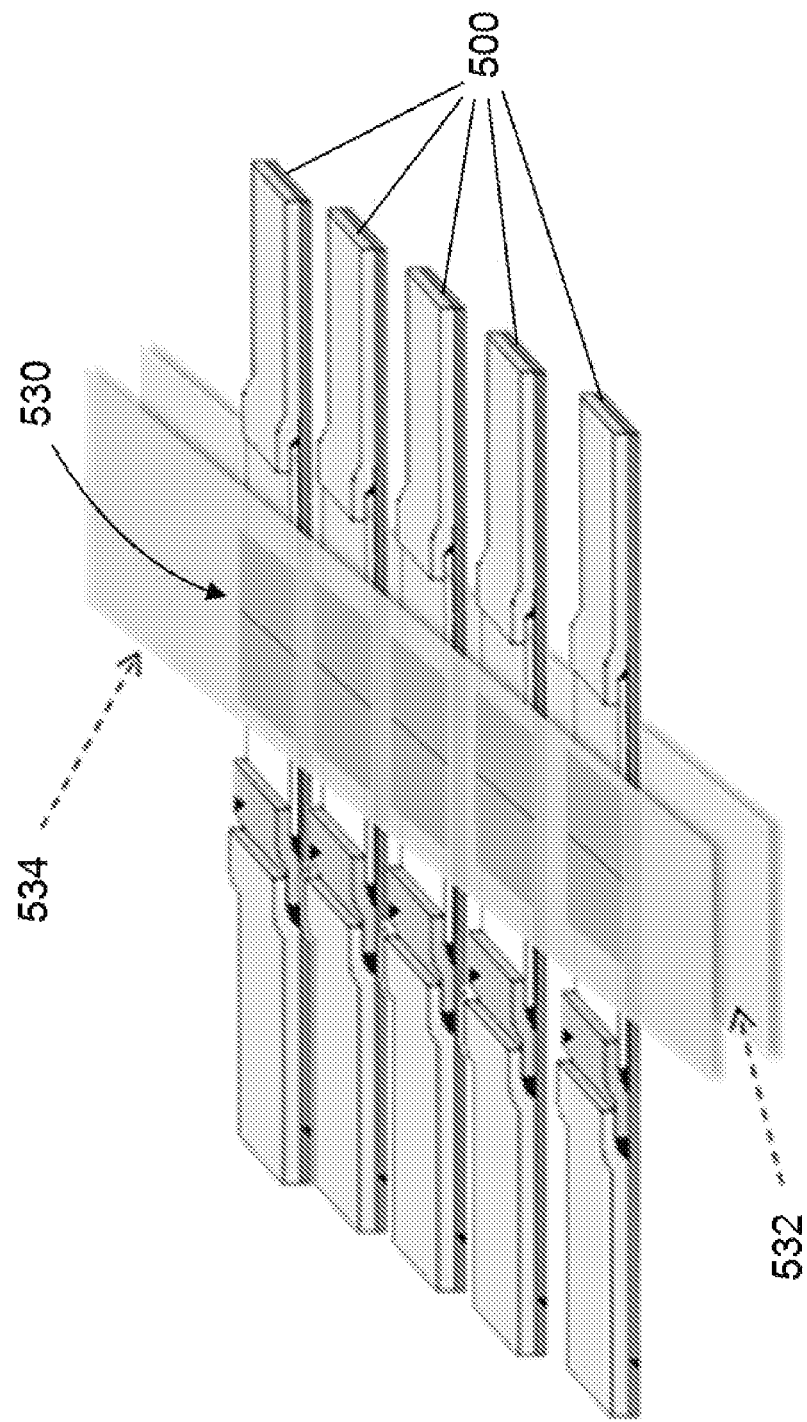
FIG. 12 is a perspective view of an array of the test strips of FIG. 5A, in accordance with an aspect of the present disclosure.

FIGS. 11 and 12 illustrate a simplified exploded arrangement of a test strip 500 and array of test strips 500 implementing the detection architecture. The finger stick point-of-care device to test human sera may use just one lateral flow test strip 500 (FIG. 11), while the skin patch configuration may use a series of lateral flow test strips 500 (FIG. 12), activated sequentially to allow biomarker levels to be continuously monitored, as well as avoid reusing the same sites for each ELISA immunoassay. The test strip 500 includes a sample pad 502 on the side contacting the skin and receiving the biofluid 501. A sample pad 502 is attached to an optically transparent backing 504. A conjugate pad 506 having fluorescent labeled secondary antibodies is disposed between the sample pad 502 and the backing 504 and receives and transports the biofluid by capillary action. A lateral flow microfluidics layer 508 having an integrated fluorescent biorecognition microarray 510 is in fluid communication with the conjugate pad 506 and receives the biofluid (containing biomarkers in the form of marked proteins, antibodies, and/or pathogens) therefrom. An OLED array 512 receiving an electrical signal from a pulse generator 514 is disposed outside the backing 504 in alignment with the microarray 510. The OLED array 512 has the same layout as the microarray 510—that is, the arrangement of OLED pixels in the OLED array 512 aligns with the arrangement of biorecognition sites in the microarray 510. The OLED array 512 is separated from the backing 504 by a bandpass optical filter 516 that filters incident light so that only the desired wavelengths of light, such as blue light in the illustrated example, pass into the microarray 510.

On the skin side of the microfluidics layer 508, a long pass optical filter 518 and a photodiode array 520 are in alignment with the microarray 510 and receive the light passing through the microarray 510 from the OLED array 512. In particular, the arrangement of photodiodes in the photodiode array aligns with the arrangement of biorecognition sites in the microarray 510. The long pass optical filter 518 filters the wavelengths of light that the bandpass optical filter 516 allows through. Thus, only light that is emitted from fluorescing biomarkers in the microarray 510 impinges the photodiode array 520. A detector 522 receives the signals from the photodiodes in the photodiode array 520 and processes them as described above. As shown in FIG. 5B, the detecting region 530 including the microarray 510 is encapsulated by a continuous flexible OLED display layer 532 containing the OLED array 512, and a continuous flexible photodiode sensor layer 534 containing the photodiode array 520.

It should be appreciated that in aspects where the photodiode array and the OLED array are described with relation to the skin, the photodiode array and the OLED array, and associated filters or polarizers, can be swapped so that they are on opposite sides of the microfluidics layer.

The modular design of the detection architecture is readily scalable from a single lateral flow test strip in the fingerstick point-of-care device to multiple lateral flow strips in a smart bandage by simply increasing the size of the flex electronics assembly and the number of test strips that are punched out. Large area flexible electronics technology is also especially appealing for the skin patch application given the need for the skin patch to bend or flex while being worn over the course of the day. Additionally, conventional rigid substrate based-electronics are typically quite fragile and can shatter into sharp fragments. This can pose a problem in this diagnostic application where the biosensor needs to come in direct contact with human skin.

Another advantageous aspect of the scalability of the present detection architecture is that the flex electronics layer or layers can be increased or extended in size to provide additional diagnostic functionality. For example, an Ion-Sensitive Field Effect Transistor (ISFET) biosensor array could be integrated on the OLED flex substrate to identify biomarkers or pathogens that are easier to detect chemically using ISFETs. Large area flexible electronics substrates are also especially appealing for ISFET technology, principally because the large size enables orders of magnitude larger (than conventional CMOS) sensing area. A large flex electronics substrate also makes it easier to integrate area intensive chemical and biological recognition material, as well as allow for a much larger number of unique biological and chemical recognition sites. The ability to apply multi-sensor site array technology is advantageous for continuous monitoring because many of today's microelectronic-scale biosensors can essentially only be used once. Regeneration methods have been reported and they may ultimately be viable, but thin-film biosensor array technology is shown herein to be a more presently viable option.

The ability to detect biomarkers in minimally invasive (blood) or non-invasive biofluids (sweat, saliva, or urine) with a high sensitivity and specificity for a given disease provides patients and clinicians real time clinical information. The present devices may detect diseases prior to the onset of clinical symptoms as well as monitor for disease progression and recurrence. Biomarkers are extremely valuable tools that can predict the state of a disease, recurrence rates, and responses to therapeutics. For example, detection of antibody responses to infectious disease, and emerging biomarkers now for cancer, may be used to rapidly identify patients for targeted treatment. The identification of proteins or peptides in patient sera have been challenged by the difficulty in identifying small quantities of protein fragments within complex protein mixtures, protein instability, and natural variations in protein content within patient populations. In contrast, antibodies in a patient's serum are highly stable indicators of a disease state and can be characterized via biochemical analysis. For example, the antibodies can be compared to records in the publicly available plasmid repository (DNASU) currently containing more than 250,000 genes in flexible expression vectors that are fully sequence-verified across human, viral and bacterial genomes. These novel proteomics approaches have been widely used for biomedical research, including the recent discovery of a panel of antibody biomarkers that may aid the early diagnosis of breast, ovarian, and HPV related cancer.

The flexible electronics and display technology used for this work is a very thin and transparent sheet of plastic, approximately the same thickness as a sheet of paper and constructed by sequentially layering and patterning nanometer-scale thin films. This approach allows the electronics functionality to be built or integrated directly into plastic substrates using active thin film devices (e.g., OLED emitters, PiN photodiodes, and TFTs), as opposed to separately bonding a large number of discrete electronic components. This approach also leverages the inherent massive technology scaling advantages of commercial flat panel display technology, which can now manufacture displays on Genii sized glass substrates that approach 10 m$^2$. This has the potential to reduce un-functionalized sensor costs to pennies per cm$^2$, which is key for low cost disposable applications. Perhaps more importantly, the flat panel display industrial base is already well established and capable of annually supplying the massive numbers of large area electronics components required to rapidly transition this technology from the laboratory to a high volume, low cost consumer product. For perspective, flat panel displays in 2012 were manufactured at a rate of 100 square kilometers per year. If just one percent (1%) of the existing flat panel industrial capacity was diverted to manufacture point-of-care devices, approximately 400 million (~25 cm$^2$) smart bandages could be manufactured annually.

Conceptually, the approach used to make a display flexible is straightforward. The flexible display manufacturing process is essentially identical to the process used to manufacture large commercial flat-panel LCD displays on glass substrates. To make the device flexible, the starting glass substrate is replaced with a 125 μm thick DuPont Teijin Films Teonex® polyethylene naphthalate (PEN) flexible plastic substrate temporarily bonded to a rigid alumina carrier. After the thin film process steps are completed, the flexible plastic PEN substrate with patterned thin film layers on top is simply peeled off, similar to peeling off a Post-It® brand note. The temporary rigid alumina carrier allows the flexible display to be processing using unmodified, off-the-shelf, thin-film semiconductor process tooling, which can currently only handle rigid glass substrates or silicon wafers. However, to avoid exceeding the PEN plastic substrate transition temperature (i.e., avoid melting it), the maximum processing temperature throughout the entire flexible electronics process sequence is limited to a maximum of ~180° C., while typical glass substrate TFT or silicon wafer processing is >300° C.

Flexible electronics devices may be manufactured on 20 μm thick polyimide substrates as an alternative to the 125 μm thick PEN plastic substrates. For the proposed skin patch/smart bandage application, the use of polyimide substrates is appealing because they are significantly more flexible than existing PEN plastic substrates, along with allowing the use of more typical >300° C. low cost-high volume commercial display processing. The polyimide process is similar to PEN. However, instead of bonding the plastic substrate to a carrier using a temporary adhesive, polyimide is instead dispensed in liquid form directly onto the rigid substrate. The polyimide is then cured at >200° C. to drive out the solvents. At this point the polyimide+rigid substrate is ready for standard thin film processing. After the thin film process steps are completed, the flexible polyimide substrate with patterned TFT layers on top is peeled off, similar to the debonding of the PEN substrate described previously.

One application of the apparatus described herein is determining with high certainty whether an individual has taken their daily medication. Alzheimer's or dementia patients are often unable to remember taking their medication. The ability of a caretaker to confirm that the patient is taking their medication is of critical importance to their well being. In the new approach, an inert food safe biomarker may be combined with the medication, where the biomarker is excreted in sweat almost immediately after ingesting the medication. Configuring a (flexible) skin patch to detect the excreted biomarker would then provide a method to confirm whether the patient has taken their medication.

Another application for flexible biosensors is a disposable smart bandage applied directly to the skin surface on the lower extremities of diabetic patients to detect the formation of pressure ulcers, or to monitor for infection in existing ulcers. Knight et al. reported that the lactate concentration in human sweat can change in response to the breakdown of soft tissue during the formation of pressure sores, common to diabetic patients. Derbyshire et al. later described a biosensor that could be applied to the skin surface to monitor lactate levels in human sweat as a indicator for pressure ulcers forming in at-risk diabetic patients.

It should be appreciated that advances in the lab-based technologies related to the on-site apparatuses and methods disclosed herein. For example, as new and improved selective binding labels and selective binding species are developed, one of ordinary skill in the art can implement them within the framework described herein.

Example 1

To further evaluate the initial viability of the optical biosensor concept, the optical configuration of FIG. 1 was assembled using a single flexible blue OLED emitter and a microscope as the optical detector. A glass slide with a drop of fluorescent green beads (10 μm microparticles G1000, available commercially from Thermo Scientific) was used as a substitute for the labeled fluorescent immunocomplex in the microfluidic detection chamber. The fluorescent beads were positioned between two orthogonally crossed linear polarizers (Polarizer1 and Polarizer2), with the bottom polarizer (Polarizer1) stacked on top of the blue OLED emitter. The source light was attenuated a varying amount with varying degrees of cross polarization.

Example 2

The optical configuration of FIG. 1 was assembled as described in Example 1, with the addition of a green long pass optical filter positioned between the second polarizer (Polarizer2) and the detector. The addition of the green long pass filter significantly increased the attenuation of the source light.

Example 3

The optical configuration of FIG. 1 was assembled as described in Example 1, with bandpass filter centered at 460 nm in place of the first linear polarizer (Polarizer 1) and a green long pass optical filter in place of the crossed polarizer (Polarizer 2). The combination of filters afforded detection of emitted green fluorescence, along with significant attenuation of the source light.

Example 4

A single OLED emitter configuration was mocked up using a 515 nm green OLED test structure manufactured at the Flexible Electronics and Display Center (FEDC) at Arizona State University (ASU) to mimic the operation of one pixel in display (array) that would be used for this application. The OLED was operated in 6 Hz pulsed mode, with a 9 volt bias. This provides an instantaneous illumination intensity of 0.3 mW/mm$^2$, which is approximately 300× brighter than the OLEDs used in previously reported crossed polarizer optical biosensor (point-of-care) configurations. By pulsing the power supply, the OLED operating voltage can be increased and subsequently significantly increase the instantaneous light intensity without degrading or damaging the OLED organic layers, while a continuous DC bias above 7 volts was shown to degrade the organic layers due to current-induced, localized joule heating in the OLED organic layers.

To evaluate the ability to detect fluorescent biorecognition material, 1 μm diameter fluorescent Nile Red microsphere Fluorophores (520 nm excite/570 nm emission) were immobilized on a series of microscope slides using logarithmic scaled dilutions (in PBS) from 1:100 to 1:1,000,000. A simple 3D printed assembly was designed and fabricated to align the center of the microscope slides with a Chroma optical filter set. The green OLED emitter was mounted in the base with a 520 nm/40 nm band pass Chroma optical filter positioned on top, and a 605 nm/70 nm band pass Chroma optical filter mounted in a groove above the slot used for the microscope slides. A proposed modification to this configuration includes depositing the thin film layers used for the optical (interference) filters on optically transparent flex substrates. This preserves flexibility for the entire smart bandage assembly—plus this approach is also expected to reduce the additional cost associated with using separate optical filters, along with reducing the thickness of the overall assembly, which is expected to further improve sensor performance.

Figure 13:
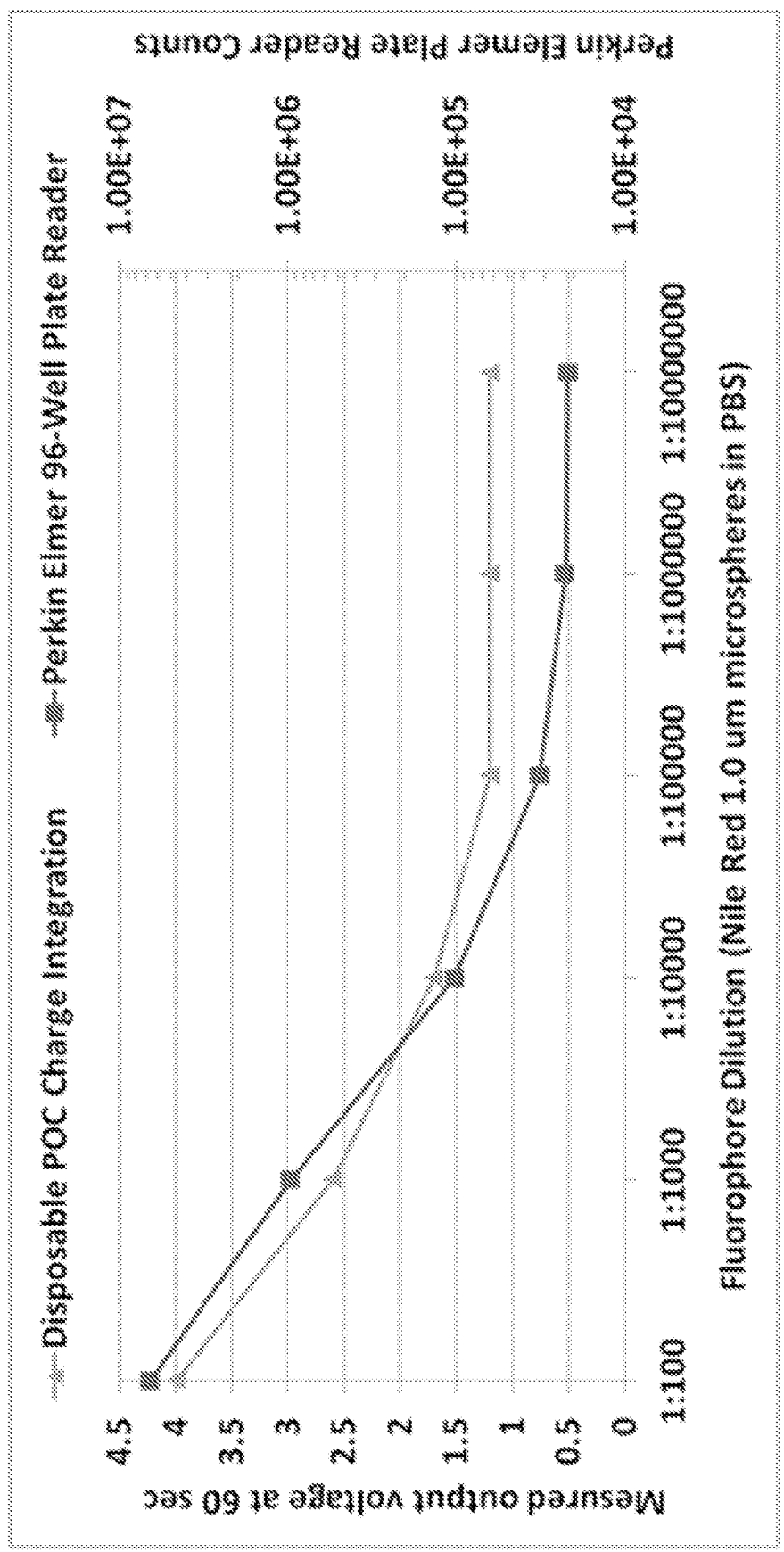
FIG. 13 is a plot comparing the detection capabilities of an apparatus of the present disclosure with a commercial detection device.

Using this optical configuration, the sensitivity of the low cost point-of-care assembly was compared to a $100,000 Perkin-Elmer 2104 96-well plate reader, using the same Nile Red Fluorophore dilutions in a 96-well plate. The simple (and very inexpensive) op-amp integrator circuit illustrated in FIG. 9 was used for signal readout in the simple point-of-care test configuration. As illustrated in FIG. 13, the low cost (disposable) point-of-care configuration successfully measured fluorophore dilutions down to 1:100,000, while the diagnostic laboratory-grade Perkin Elmer 96-well plate reader detected dilutions down to about 1:1,000,000. This indicates that the $100,000 Perkin Elmer 96-well plate reader is barely 10× more sensitive than our few dollar disposable point-of-care concept configuration, which indicates that our proposed configuration will certainly be quite sensitive.

The present disclosure has been described in terms of one or more preferred aspects, and it should be appreciated that many equivalents, alternatives, variations, and modifications, aside from those expressly stated, are possible and within the scope of the invention.

We claim:

1. An apparatus for detecting or quantifying a plurality of analytes of interest in a fluid sample suspected of containing the plurality of analytes of interest, the apparatus comprising:
   a microfluidic or nanofluidic system comprising:
      a sample inlet that, in use, receives the fluid sample;
      a mixing chamber that, in use, mixes the sample with one or more selective binding fluorescent labels;
      a detection chamber comprising a first volume and a second volume, the first volume comprising a first immobilized selective binding species and the second volume comprising a second immobilized selective binding species; and
      a sample outlet, wherein the sample inlet, the mixing chamber, the detection chamber, and the sample outlet are fluidly connected;
   and
   an optical system comprising:
      a light source configured to illuminate the first volume and the second volume;
      an optical detector configured to receive and detect emitted radiation from the first volume and the second volume; and
      a light source attenuator positioned between the detection chamber and the optical detector.

2. The apparatus of claim 1, wherein the system is operable to detect or quantify a first analyte of interest and a second analyte of interest, wherein
   the first immobilized selective binding species selectively binds the first analyte of interest and not the second analyte of interest and the second immobilized selective binding species binds the second analyte of interest and not the first analyte of interest.

3. The apparatus of claim 1, wherein the system is operable to detect or quantify a first analyte of interest and a second analyte of interest, wherein a first selective binding label selectively binds the first analyte of interest and not the second analyte of interest and a second selective binding label selectively binds the second analyte of interest and not the first analyte of interest.

4. The apparatus of claim 1, wherein the light source is configured to illuminate the first volume with light having a first illumination spectrum and the second volume with light having a second illumination spectrum.

5. The apparatus of claim 1, wherein the optical detector is configured to receive and detect emitted radiation from the first volume having a first emission spectrum and emitted radiation from the second volume having a second emission spectrum.

6. The apparatus of claim 1, wherein the light source is an organic light emitting diode array.

7. The apparatus of claim 1, wherein the optical detector is a PiN photodiode array.

8. The apparatus of claim 1, wherein the light source and the optical detector each comprise thin-film transistor arrays.

9. An apparatus for detecting or quantifying a plurality of analytes of interest in a fluid sample suspected of containing the plurality of analytes of interest, the apparatus comprising:

a microfluidic or nanofluidic system comprising:

a sample inlet that, in use, receives the fluid sample;

a mixing chamber that, in use, mixes the sample with one or more selective binding fluorescent labels;

a detection chamber comprising a first volume and a second volume, the first volume comprising a first immobilized selective binding species immobilized to an inner surface of the detection chamber and the second volume comprising a second immobilized selective binding species immobilized to the inner surface of the detection chamber; and a sample outlet, wherein the sample inlet, the mixing chamber, the detection chamber, and the sample outlet are fluidly connected;

and an optical system comprising:

a light source configured to illuminate the first volume and the second volume;

an optical detector configured to receive and detect emitted radiation from the first volume and the second volume; and a light source attenuator positioned between the detection chamber and the optical detector.

* * * * *